(12) United States Patent
Nash et al.

(10) Patent No.: US 7,517,524 B2
(45) Date of Patent: Apr. 14, 2009

(54) IMMUNOINTERACTIVE MOLECULES

(75) Inventors: Andrew Nash, Kew (AU); Giuseppe Maccarone, Pascoe Vale (AU); Pierre David Scotney, Greensborough (AU)

(73) Assignee: Zenyth Operations Pty Ltd (AU)

( * ) Notice: Subject to any disclaimer, the term of this patent is extended or adjusted under 35 U.S.C. 154(b) by 0 days.

(21) Appl. No.: 11/652,711

(22) Filed: Jan. 12, 2007

(65) Prior Publication Data
US 2007/0128197 A1 Jun. 7, 2007

Related U.S. Application Data

(63) Continuation of application No. 10/440,295, filed on May 16, 2003, now abandoned.

(60) Provisional application No. 60/381,285, filed on May 17, 2002.

(51) Int. Cl.
A61K 39/395 (2006.01)
C12P 21/08 (2006.01)
C07K 16/00 (2006.01)
C07K 16/18 (2006.01)
C07K 16/22 (2006.01)

(52) U.S. Cl. .............. 424/130.1; 424/133.1; 424/141.1; 424/142.1; 424/145.1; 435/70.21; 530/387.1; 530/387.3; 530/388.15; 530/388.25

(58) Field of Classification Search .................. None
See application file for complete search history.

(56) References Cited

U.S. PATENT DOCUMENTS

| | | | |
|---|---|---|---|
| 5,260,203 | A | 11/1993 | Ladner et al. |
| 5,530,101 | A | 6/1996 | Queen et al. |
| 6,331,301 | B1 | 12/2001 | Eriksson et al. |

FOREIGN PATENT DOCUMENTS

| | | | |
|---|---|---|---|
| WO | WO96/26736 | * | 9/1996 |
| WO | WO 96/34096 | | 10/1996 |

OTHER PUBLICATIONS

Rudikoff et al, Proc Natl Acad Sci USA vol. 79: 1979-1983, 1982.*
Barrios et al, J Molecular Recognition 17: 332-338, 2004.*
Kobrin et al, J Immunology 146: 2017-2020, 1991.*
Altschul, et al., "Gapped Blast and PSI-Blast: a new generation of protein database search programs", *Nucl. Acids Res.* 25:3389-3402 (1997).
Ausubel, et al., "Mapping by Partial Endonuclease Digestions", *Current Protocols in Molecular Biology*, John Wiley & Sons Inc. Chapter 15 Unit 3.3 (1992).
Beaucage, et al., "Deoxynucleoside Phosphoramidites—A New Class of Key Intermediates for Deoxypolynucleotide Synthesis", *Tetrahedron Letters* 22(20):1859-1862 (1981).
Bellomo, et al., "Mice Lacking the Vascular Endothelial Growth Factor-B Gene (Vegfb) Have Smaller Hearts, Dysfunctional Coronary Vasculature and Impaired Recovery From Cardiac Ischemia", *Circulation Research* 86(2): E29-35 (2000).
Bonner, et al., "A Film Detection Method for Tritium-Labelled Proteins and Nucleic Acids in Polyacrylamide Gels", *Eur. J. Biochem.* 46: 83-88 (1974).
Brown, et al., "VEGF induces airway epithelial cell proliferation in human fetal lung in vitro", *Am. J. Physiol Lung Cell Mol. Physiol,* 281: L1001-L1010 (2001).
Clauss, et al., "The Vascular Endothelial Growth Factor Receptor Flt-1 Mediates Biological Activities", *The Journal of Biological Chemistry*, 271(30): 17629-17634 (1996).
Fiers, et al., "Complete nucleotide sequence of SV40 DNA", *Nature,* 273: 113-120 (1978).
Grimmond, et al., "Cloning and Characterization of a Novel Human Gene Related to Vascular Endothelial Growth Factor", *Genome Research*, 6 124-131 (1996).
Gunningham, et al., "VEGF-B expression in human primary breast cancer is associated with lymph node metastasis but not angiogenesis", *J. Pathol*, 193(3):325-332 (2001).
Johnson, et al., "Cytotocicity of a Replication-Defective Mutant of Herpes Simplex Virus Type 1", *Journal of Virology*, 66(5):2952-2965 (1992).
Kasama, et al., "Vascular Endothelial Growth Factor Expression by Activated Synovial Leukocytes in Rheumatoid Arthritis", *Arthritis & Rheumatism* 44(11): 2512-2524 (2001).
Kohler, et al., "Derivation of specific antibody-producing tissue culture and tumor lines by cell fusion", *Eur. J. Immunol.*, 6: 511-519 (1976).
Kohler, et al., "Continuous cultures of fused cells secreting antibody of predefined specificity", *Nature*, 256: 495-499 (1975).
Kubo, et al., "Location of a region of the muscarinic acetylcholine receptor involved in selective effector coupling", *FEBS Lett.* 241(1-2): 119-125 (1988).
Kyte, et al., "A Simple Method for Displaying the Hydropathic Character of a Protein", *J. Mol. Biol.* 157: 105-132 (1982).
Li, et al., "Isoform-specific Expression of VEGF-B in Normal Tissues and Tumors", *Growth Factos* 19: 49-59 (2001).

(Continued)

*Primary Examiner*—Phuong Huynh
(74) *Attorney, Agent, or Firm*—Scully, Scott, Murphy & Presser, P.C.

(57) ABSTRACT

The present invention relates generally to immunointeractive molecules and more particularly antibodies which bind to vascular endothelial growth factor-B (VEGF-B) or its functional or structural equivalent and inhibit the biological activity of VEGF-B. In particular, the present invention relates to deimmunized such as humanized or human antibodies that bind to VEGF-B and inhibit the biological activity of VEGF-B. These antibodies have uses in the treatment or prevention of diseases associated with perturbations in normal vasculogenesis or angiogenesis or vascular remodelling. The present invention further contemplates a method of modulating diseases associated with perturbations in normal vasculogenesis or angiogenesis or vascular remodelling by the administration of the subject antibodies. The present invention further provides an assay system useful for identifying antibodies which bind to VEGF-B and block the biological activity of VEGF-B. Accordingly, a method of screening for inhibitors of the biological activity of VEGF-B is also provided.

6 Claims, 18 Drawing Sheets

OTHER PUBLICATIONS

Liu, et al. "Vascular Endothelial Growth Factor Is Increased in Ascites from Metastatic Pancreatic Cancer", *Journal of Surgical Research* 102: 31-34 (2002).

Ma, et al., "Identification of the ligand-binding domain of human vascular-endothelial-growth-factor receptor Flt-I", *Biotechnol. Appl. Biochem*. 34: 199-204 (2001).

Makinen, et al., "Differential Binding of Vascular Endothelial Growth Factor B Splice and Proteolytic Isoforms to Neuropilin-1", *The Journal of Biological Chemistry*, 274(30): 21217-21222 (1999).

Marmur, et al., "Determination of the Base Composition of Deoxyribonucleic Acid from its Thermal Denaturation Temperature", *J. Mol. Biol.*, 5:109-118 (1962).

Matteucci, et al., "Synthesis of Deoxyoligonucleotide on a Polymer Support", *J. Am. Chem. Soc.*, 103: 3185-3191 (1981).

Matthies, et al., "Neuropilin-1 Participates in Wound Angiogenesis", *American Journal of Pathology* 160(1): 289-296 (2002).

Nicholson, et al., "Suppressor of cytokine signaling-3 preferentially binds to the SHP-2-binding site on the shared cytokine receptor subunit gp130", *PNAS* 97(12) 6493-6498 (2000).

Niida, et al., "Vascular Endothelial Growth Factor Can Substitute for Macrophage Colony-stimulating Factor in the Support of Osteoclastic Bone Resorption", *J. Exp. Med*. 190(2): 293-298 (1999).

Rich, et al., "Correlations Between Basic Fibroblast Growth Factor (bFGF), Vascular Endothelial Growth Factor (VEGF), and Clinical Features of Pulmonary Arterial Hypertension (PAH)", *The Journal of Heart and Lung Transplantation*, 21(1): 159 (2002).

Scrofani, et al., "Purification and refolding of vascular endothelial growth factor-B", *Protein Science*, 9:2018-2025 (2000).

Street, et al., "The angiogenic response to skeletal injury is preserved in the elderly", *Journal of Orthopaedic Research* 19: 1057-1066 (2001).

Townson, et al., "Characterization of the Murine VEGF-Related Factor Gene", *Biochemical and Biophysical Research Communications* 220: 922-928 (1996).

Tuder, et al., "Expression of angiogenesis-related molecules in plexiform lesions in severe pulmonary hypertension: evidence for a process of disordered angiogenesis", *Journal of Pathology* 195:367-374 (2001).

Wang, et al., "Vascular Endothelial Growth Factor Upregulates the Expression of Matrix Metalloproteinases in Vascular Smooth Muscle Cells", *Circ. Res.*, 83: 832-840 (1998).

Weismann, et al., "Crystal Structure at 1.7 A Resolution of VEGF in Complex with Domain 2 of the Flt-1 Receptor", *Cell* 91: 965-704 (1997).

Dr. Andrew Nash, "Therapeutic angiogenesis-laboratory and clinical issues", PowerPoint Presentation, presented at the 35th Annual Scientific Meeting of the Australian Society of Clinical and Experimental Pharmacologists and toxicologists, Dunedin, New Zealand, (Dec. 3-5, 2001).

Scotney, P.D., et al., "Human Vascular Endothelial Growth Factor B: Characterization of Recombinant Isoforms and Generation of Neutralizing Monoclonal Antibodies", *Clinical and Experimental Pharmacology and Physiology*, 29: 1024-1029, (2002).

Gura et al., Science 278: 1041-1042, Nov. 1997.

Dermer, Bio/Technology 12: 320, 1994.

Harlow et al., in Antibodies a Laboratory Manual, 1988, Cold Spring harbor laboratory publication, Cold Spring Harbor, NY pp. 141-149, pp. 626-629.

Stryer et al., in Biochemistry, Third edition, W H Freeman Company, New York, pp. 31-33, 1998.

Attwood et al., The Babel of Bioinformatics, 2000, Science 290(5491): 471-473.

Skolnick et al., From genes to protein structure and function: novel applications of computational approaches in the genomic era, Jan. 2000, Trends in Biotech. 18(1):34-39.

* cited by examiner

```
ATGGTTCTTGCCAGCTCTACCACCAGCATCCACACCATGCTGCTCCTGATGCTCTTCCACCTGGGACTCCAAGC
              +         +         +         +         +         +         +         +
                                                                                    80
TACCAAGAACGGTCGAGATGGTGGTCGTAGGTGGTGCTAGGACGAGGACTACGAGAGAAGGTGGACCCTGAGGTTCG

M  V  L  A  S  S  T  T  S  I  H  T  M  L  L  L  M  L  F  H  L  G  L  Q  A
                          IL3 signal sequence TTCAATCTCGGGCGCGCCAGGACTACAAGGACGACGATGACAAGAGACGCGCCAGTCTAGTTCAGGTTCAAAATTAAAAGATC
              +         +         +         +         +         +         +         +
                                                                                   160
AAGTTAGAGCCCGCGCGGTCCTGATGTTCCTGCTGCTACTGTTCTCTGCGCGGTCAGATCAAGTCCAAGTTTTAATTTTCTAG S  I  S  A  R  Q  D  Y  K  D  D  D  D  K  T  R  Q  S  S  G  S  K  L  K  D
 -IL3 signal s           FLAG tag                         hFLT1 (domains 1-4)

CTGAACTGAGTTTAAAAGGCACCCAGACACTGCAAGCAGGCCAGACACTGCATCTCCAATGCAGGGGGAAGCAGCC
              +         +         +         +         +         +         +         +
                                                                                   240
GACTTGACTCAAATTTTCCGTGGGTCTGTGACGTTCGTCCGGTCTGTGACGTAGAGGTTACGTCCCCCTTCGTCGG

P  E  L  S  L  K  G  T  Q  H  I  M  Q  A  G  Q  T  L  H  L  Q  C  R  G  E  A  A
                                      hFLT1 (domains 1-4)

CATAAATGGTCTTTGCCTGAAATGGTGAGTAAGGAAAGCGAAAGGCTGAGCATAAATCTGCCTGTGAAGAAATGG
              +         +         +         +         +         +         +         +
                                                                                   320
GTATTTACCAGAACGGACTTTACCACTCATTCCTTCGCTTTCCGACTCGTATTGATTTAGACGGACACCTTCTTTACC

H  K  W  S  L  P  E  M  V  S  K  E  S  E  R  L  S  I  T  K  S  A  C  G  R  N  G
                                      hFLT1 (domains 1-4)
```

Figure 4

```
CAAACAATTCTGCAGTACTTTAACCTTGAACACAGCTCAAGCAAACCACACTGGCTTCTACAGCTGCAAATATCTAGCTG
         +         +         +         +         +         400
GTTTGTTAAGACGTCATGAAATTGGAACTTGTGTCGAGTTCGTTTGGTGTGACCGAAGATGTCGACGTTTATAGATCGAC

K  Q  F  C  S  T  L  T  L  N  T  A  Q  A  N  H  T  G  F  Y  S  C  K  Y  L  A
                           ————hFLT1 (domains 1-4)————

TACCTACTTCAAAGAAGAAGGAAACAGAATCTGCAATCTATATATTTATTAGTGATACAGGTAGACCTTTCGTAGAGATG
         +         +         +         +         +         480
ATGGATGAAGTTTCTTCTTCCTTTGTCTTAGACGTTAGATATATAAATCACTATGTCCATCTGGAAAGCATCTCTAC

V  P  T  S  K  K  K  E  T  E  S  A  I  Y  I  F  I  S  D  T  G  R  P  F  V  E  M
                          ————hFLT1 (domains 1-4)————

TACAGTGAAATCCCCGAAATTATACACACATGACTGAAGGAAGGAGCTCGTCATTCCCTGCCGGGTTACGTCACCTAACAT
         +         +         +         +         +         560
ATGTCACTTTAGGGGCTTTAATATGTGTGTACTGACTTCCTCCTCGAGCAGTAAGGGACGGCCCAATGCAGTGGATTGTA

Y  S  E  I  P  E  I  I  H  M  T  E  G  R  E  L  V  I  P  C  R  V  T  S  P  N  I
                          ————hFLT1 (domains 1-4)————

CACTGTTACTTTAAAAAAGTTTCCACTTGACACTTTGATCCCTGATGGAAAACGCATAATCTGGGACAGTAGAAAGGGCT
         +         +         +         +         +         640
GTGACAATGAAATTTTTTCAAAGGTGAACTGTGAAACTAGGACTAGGGACTACCTTTTGCGTATTAGACCCTGTCATCTTTCCCGA

T  V  T  L  K  K  F  P  L  D  T  L  I  P  D  G  K  R  I  I  W  D  S  R  K  G
                          ————hFLT1 (domains 1-4)————
```

Figure 4 (continued)

```
TCATCATATCAAATGCAACGTACAAAGAAATAGGGCTTCTGACCTGTGAAGCAACAGTCAATGGGCATTTGTATAAGACA
      +         +         +         +         +         +         +         +    720
AGTAGTATAGTTTACGTTGCATGTTTCTTTATCCCGAAGACTGGACACTTCGTTGTCAGTTACCCGTAAACATATTCTGT
  F   I   I   S   N   A   T   Y   K   E   I   G   L   L   T   C   E   A   T   V   N   G   H   L   Y   K   T
                                              ────────── hFLT1 (domains 1-4) ──────────

AACTATCTCACACATCGACAAACCAATACAATCATAGATGTCCAAATAAGCACACCAGTCAAATTACTTAGAGG
      +         +         +         +         +         +         +         +    800
TTGATAGAGTGTGTAGCTGTTTGGTTATGTTAGTATCTACAGGTTTATTCGTGTGGTGCGGGTCAGTTTAATGAATCTCC
  N   Y   L   T   H   R   Q   T   N   T   I   I   D   V   Q   I   S   T   P   R   P   V   K   L   L   R   G
  ────────────────────────────────────── hFLT1 (domains 1-4) ──────────────────────────────────────

CCATACTCTTGTCCTCAATTGTACTGCTACCACTCCCTTGAACACGAGAGTTCAAATGACCTGGAGTTACCCTGATGAAA
      +         +         +         +         +         +         +         +    880
GGTATGAGAACAGGAGTTAACATGACGATGGTGAGGGAACTTGTGCTCTCAAGTTTACTGGACCTCAATGGGACTACTTT
  H   T   L   V   L   N   C   T   A   T   T   P   L   N   T   R   V   Q   M   T   W   S   Y   P   D   E
  ──────────────────────────────────── hFLT1 (domains 1-4) ─────────────────────────────────────

AAAATAAGAGAGTTTCCGTAAGGCGACGAATTGACCAAAGCAATTCCCATGCCAACATATTCTACAGTGTTCTTACTATT
      +         +         +         +         +         +         +         +    960
TTTTATTCTCTCGAAGGCATTCCGCTGCTTAACTGGTTCGTTAAGGTACGGTTGTATAAGATGTCACAAGAATGATAA
  K   N   K   R   A   S   V   R   R   R   I   D   Q   S   N   S   H   A   N   I   F   Y   S   V   L   T   I
  ──────────────────────────────────── hFLT1 (domains 1-4) ─────────────────────────────────────
```

Figure 4 (continued)

```
GACAAAAATGCAGAACAAAGACAAAGGACTTTATACTTGTCGTGTAAGGAGTGGACCATCATTCAAATCTGTTAACACCTC
     +         +         +         +         +         +         +         +       1040
CTGTTTTACGTCTTGTTTCTGTTTCCTGAAATATGAACAGCACATTCCTCACCTGGTAGTAAGTTTAGACAATTGTGGAG
 D   K   M   Q   N   K   D   K   G   L   Y   T   C   R   V   R   S   G   P   S   F   K   S   V   N   T   S
                                                  hFLT1 (domains 1-4)

AGTGCATATATATGATAAAGCATTCATCACTGTGAAACATCGAAAACAGCAGGTGCTTGAAACCGTAGCTGGCAAGCGGT
     +         +         +         +         +         +         +         +       1120
TCACGTATATATACTATTTCGTAAGTAGTGACACTTTGTAGCTTTTGTCGTCCACGAACTTTGGCATCGACCGTTCGCCA
 V   H   I   Y   D   K   A   F   I   T   V   K   H   R   K   Q   Q   V   L   E   T   V   A   G   K   R
                                                  hFLT1 (domains 1-4)

CTTACCGGCTCTCTATGAAAGTGAAGGCATTTCCCTGCCGGAAGTTGTATGGTTAAAAGATGGGTTACCTGCGACTGAG
     +         +         +         +         +         +         +         +       1200
GAATGGCCGAGAGATACTTTCACTTCCGTAAAGGGACGGCCTTCAACATACCAATTTTCTACCCAATGGACGCTGACTC
 L   T   G   S   L   *   K   V   K   A   F   P   S   P   E   V   V   W   L   K   D   G   L   P   A   T   E
 S   Y   R   L   S   M   K   V   K   A   F   P   S   P   E   V   V   W   L   K   D   G   L   P   A   T   E
                                                  hFLT1 (domains 1-4)

AAATCTGCTCGCTATTTGACTCGTGGCTACTCGTTAATTATCAAGGACGTAACTGAAGAGGATGCAGGGAATTATACAAT
     +         +         +         +         +         +         +         +       1280
TTTAGACGAGCGATAAACTGAGCACCGATGAGCAATTAATAGTTCCTGCATTGACTTCTCCTACGTCCCTTAATATGTTA
 K   S   A   R   Y   L   T   R   G   Y   S   L   I   K   D   V   T   E   E   D   A   G   N   Y   T   I
```

Figure 4 (continued)

```
CTTGCTGAGCATAAAAACAGTCAAATGTGTTTAAAAACCTCACTGCCACTCTAATTGTCAATGTGAAACCCAGATTTACG
                                                                                 1360
GAACGACTCGTATTTTGTCAGTTTACACAAATTTTTGGAGTGACGGTGAGATTAACAGTTACACTTTGGGTCTAAATGC
 L  L  S  I  K  Q  S  N  V  F  K  N  L  T  A  T  L  I  V  N  V  K  P  Q  I  Y
                              hFLT1 (domains 1-4)

AAAAGGGAGAAATTGAAGCCATAGTCGTGCCTGTTTGCTTAGCATTCCTATTGACAACTCTTCTGGGAGTGCTGTTCTGC
                                                                                 1440
TTTTCCCTCTTTAACTTCGGTATCAGCACGGACAAACGAATCGTAAGGATAACTGTTGAGAAGACCCTCACGACAAGACG
 E  K  G  E  I  E  A  I  V  V  P  V  C  L  A  F  L  L  T  T  L  L  G  V  L  F  C
    hFLT1          gp130 transmembrane domain TTTAATAAGGCGAGACCTAATTAAAAAACACATCTGGCCTAATGTTCCAGATCCTTCAAAGAGTCATATTGCCCAGTGGTC
                                                                                 1520
AAATTATTCGCTCTGGATTAATTTTTTGTGTAGACCGATTACAAGGTCTAGGAAGTTTCTCAGTATAACGGGTCACCAG
 F  N  K  R  D  L  I  K  K  H  I  W  P  N  V  P  D  P  S  K  S  H  I  A  Q  W  S
  gp1                       gp130 intracellular domain ACCTCACACTCCTCCAAGGCACAATTTTAATTCAAAAGATCAAATGTATTCAGATGGCAATTTCACTGATGTAAGTGTTG
                                                                                 1600
TGGAGTGTGAGGAGGTTCCGTGTTAAAATTAAGTTTTCTAGTTTACATAAGTCTACCGTTAAAGTGACTACATTCACAAC
 P  H  T  P  P  R  H  N  F  N  S  K  D  Q  M  Y  S  D  G  N  F  T  D  V  S  V
                  gp130 intracellular domain
```

Figure 4 (continued)

```
                                                                                                    1680
TGGAAATAGAAGCAAATGACAAAAGCCTTTTCCAGAAGATCTGAAATTATTGGACCTGTTCAAAAAGGAAAAATTAAT
————————————————+————————————————+————————————————+————————————————+————————————————
ACCTTTATCTTCGTTTACTGTTTTTCGGAAAAGGTCTTCTAGACTTTAATAACCTGGACAAGTTTTCCTTTTTAATTA

V  E  I  E  A  N  D  K  K  P  F  P  E  D  L  K  L  L  D  L  F  K  K  E  K  I  N
                                       ————————————————————————————————————————————
                                                   gp130 intracellular domain
                                                                                                    1760
ACTGAAGGACACAGCAGTGGTATTGGGGGGTCTTCATGCATGTCATCTTCTAGGCCAAGCATTTCTAGCAGTGATGAAAA
————————————————+————————————————+————————————————+————————————————+————————————————
TGACTTCCTGTGTCGTCACCATAACCCCCAGAAGTACGTACAGTAGAAGATCCGGTTCGTAAAGATCGTCACTACTTTT T  E  G  H  S  S  G  I  G  G  S  S  C  M  S  S  R  P  S  I  S  S  D  E  N
—————————————————————————————————————————————————————————————————————————————
                           gp130 intracellular domain
                                                                                                    1840
TGAATCTTCACAAAACACTTCGAGTCGTCCAGTATTCTACCGTGGTACACAGTTGGCTACAGACACCAAGTTCCGTCAG
————————————————+————————————————+————————————————+————————————————+————————————————
ACTTAGAAGTGTTTTGTGAAGCTCAGCAGGTCATAAGATGGCACCATGTCTGTGGTTCAAGGCAGTC E  S  S  Q  N  T  S  S  T  V  Q  Y  S  T  V  V  H  S  G  Y  R  H  Q  V  P  S
——————————————————————————————————————————————————————————————————————————————
                             gp130 intracellular domain
                                                                                                    1920
TCCAAGTCTTCTCAAGATCCGAGTCTACCCAGCCCTTGTTAGATTCAGAGGAGCGGCCAGAAGATCTACAATTAGTAGAT
————————————————+————————————————+————————————————+————————————————+————————————————
AGGTTCAGAAGAGTTCTAGGCTCAGATGGGTCGGGAACAATCTAAGTCTCCTCGCCGGTCTTCTAGATGTTAATCATCTA V  Q  V  F  S  R  S  E  S  T  Q  P  L  L  D  S  E  E  R  P  E  D  L  Q  L  V  D
—————————————————————————————————————————————————————————————————————————————————
                             gp130 intracellular domain
```

Figure 4 (continued)

```
CATGTGAGATGGGGGTGATGGTATTTTGCCCAGGCAACAGAACTGCAGTCAGCATGAATCCAGTCCAGA
     +         +         +         +         +         +         +        2000
GTACATCTACCGCCACTACCATAAAACGGGTCCGTTGTCTTGACGTCAGTCGTACTTAGGTCAGGTCT

H  V  D  G  G  D  G  I  L  P  R  Q  Y  F  K  Q  N  C  S  Q  H  E  S  S  P  D
                                            gp130 intracellular domain TATTTCACATTTTGAAAGGTCAAAGCAAGTCAAAGTTTCATCAGTCAATGAGGAAGATTTTGTTAGACTTAAACAGCAGATTTCAG
     +         +         +         +         +         +         +        2080
ATAAAGTGTAAAACTTTCCAGTTTCGTTCAGTTTCAAAGTAGTCAGTTACTCCTTCTAAAACAATCTGAATTTGTCGTCTAAAGTC I  S  H  F  E  R  S  K  Q  V  S  S  V  N  E  E  D  F  V  R  L  K  Q  Q  I  S
                                            gp130 intracellular domain ATCATATATTTCACAATCCTGTGGTGGGCAAATGAAAATGTTTCAGGAAGTTTCTGCAGCAGATGCTTTTGGTCCAGGT
     +         +         +         +         +         +         +        2160
TAGTATAAAGTGTTAGGACACCATAGAGACCTAGACCCGTTTACTTTTACAAAGTCCTTCAAAGACGTCGTCTACGAAAACCAGGTCCA D  H  I  S  Q  S  C  G  S  G  Q  M  K  M  F  Q  E  V  S  A  A  D  A  F  G  P  G
                                            gp130 intracellular domain
```

Figure 4 (continued)

```
ACTGAGGGACAAGTAGAAACAGTTGGCAGGCATGCCTGACTGATGAAGGCATGCCTAAAAGTTACTTACC
                                                                              2240
TGACTCCCTGTTCATCTTTCTAAACTTTGTCAACCGTACCTCCGACGCTGACTACTTCCGTACGGATTTTCAATGAATGG

T  E  G  Q  V  E  R  F  E  T  V  G  M  E  A  A  T  D  E  G  M  P  K  S  Y  L  P
 ───────────────────────────────gp130 intracellular domain─────────────────────────

ACAGACTGTACGGCAAGGCGGCTACATGCCTCAGTGA
                                      2277
TGTCTGACATGCCGTTCCGCCGATGTACGGAGTCACT

Q  T  V  R  Q  G  G  Y  M  P  Q
 ─────gp130 intracellular domain─
```

Figure 4 (continued)

```
ATGGTTCTTGCCAGCTCTACCACCAGCATCCACACCATGCTGCTCCTGATGCTCTTCCACCTGGGACTCCAAGC
      +---------+---------+---------+---------+---------+---------+---------+  80
TACCAAGAACGGTCGAGATGGTGGTCGTAGGTGTGGTACGACGAGGACGAGGACTACGAGAAGGTGGACCCTGAGGTTCG

M  V  L  A  S  S  T  T  S  I  H  T  M  L  L  L  M  L  F  H  L  G  L  Q  A
                 └─────────────── murine il3 ss ──────────────────────────────

TTCAATCTCGGCGCGCCAGGACTACAAGGACGATGACAAGACGCGCCAGTCTAGTTCAGGTTCAAAATTAAAAGATC
      +---------+---------+---------+---------+---------+---------+---------+ 160
AAGTTAGAGCCGCGCGGTCCTGATGTTCCTGCTACTGTTCTGCGCGGTCAGATCAAGTCCAAGTTTTAATTTTCTAG

S  I  S                  A  R  Q  D  Y  K  D  D  D  D  K  T  R  Q  S  S  G  S  K  L  K  D
  ── murine il3 ss ─┘     └────────────── FLAG ────────────┘└────── hFLT1 (domain 1-3).

AAGTTAGAGCCGCGCGGGTCCTGATGTTCCTGCTACTGTTCTGCGCGGTCAGATCAAGTCCAAGTTTTAATTTTCTAG
      +---------+---------+---------+---------+---------+---------+---------+ 240
CTGAACTGAGTTTAAAAGGCACCCAGACTGAAATGGTGAGTAAGGAAAGCGAAGGCTGAGCATAACTAAATCTGCCTGTGGAAGAAATGG

P  E  L  S  L  K  G  T  Q  H  I  M  Q  A  G  Q  T  L  H  L  Q  C  R  G  E  A  A
                                        └──────────── hFLT1 (domain 1-3). ────────

GACTTGACTCAAATTTTCCGTGGGTCGATTTACCACTCATTCGCTTCCAGACTCGTATTGATTAGACGGACACCTTCTTACC
      +---------+---------+---------+---------+---------+---------+---------+ 320
CATAAAATGGTCTTTGCCTGAAATGGTGAGTAAGGAAAGCGAAGGCTGAGCATAACTAAATCTGCCTGTGGAAGAAATGG

GTATTTACCAGAAACGGACTTACCACTCATTCCGCTTCCAGACTCGTATTGATTAGACGGACACCTTCTTACC

H  K  W  S  L  P  E  M  V  S  K  E  S  E  R  L  S  I  T  K  S  A  C  G  R  N  G
                                         └────────── hFLT1 (domain 1-3). ──────────
```

Figure 5

```
CAAACCAATTCTGCAGTACTTTAACCTTGAACACACAGCTCAAGCAAACCACACTGGCTTCTACAGCTGCAAATATCTAGCTG
         +         +         +         +         +         +         +         +      400
GTTTGTTAAGACGTCATGAAATTGGAACTTGTGTGTCGAGTTCGTTGGTGTGACCGAAGATGTCGACGTTTATAGATCGAC

K  Q  F  C  S  T  L  T  L  N     T  A  Q  N  H     T  G  F  Y  S  C  K  Y  L  A
                                 hFLT1 (domain 1-3).

TACCTACTTCAAAGAAGAAGGAAACAGAATCTGCAATCTATATATTTATTAGTGATACAGGTAGACCTTTCGTAGAGATG
         +         +         +         +         +         +         +         +      480
ATGGATGAAGTTTCTTCTTCCTTTGTCTTAGACGTTAGATATAAATAATCACTATGTCCATCTGGAAAGCATCTCTAC

V  P  T  S  K  K  K  E  T  E  S  A  I  Y  I  F     I  S  D  T  G  R  P  F  V  E  M
                                 hFLT1 (domain 1-3).

TACAGTGAAATCCCCGAAATTATACACATGACTGAAGGAAGGGAGCTCGTCATTCCCTGCCGGGTTACGTCACCTAACAT
         +         +         +         +         +         +         +         +      560
ATGTCACTTTAGGGGCTTTAATATGTGTACTGACTTCCTTCCCTCGAGCAGCAGTAAGGGACGGCCCAATGCAGTGGATTGTA

Y  S  E  I  P  E  I  I  H  M  T  E  G  R  E  L     V  I  P  C  R  V  T  S  P  N  I
                                 hFLT1 (domain 1-3).

CACTGTTACTTTAAAAAAGTTTCCACTTGACACTTTGATCCCTGATGGAAAACGCATAATCTGGGACAGTAGAAAGGGCT
         +         +         +         +         +         +         +         +      640
GTGACAATGAAATTTTTTCAAAGGTGAACTGTGAAACTAGGGACTACCTTTTGCGTATTAGACCCTGTCATCTTTCCCGA

T  V  T  L  K  K  F  P  L  D     T  L  I  P  D  G     K  R  I  I  W  D  S  R  K  G
                                 hFLT1 (domain 1-3).
```

Figure 5 (continued)

```
TCATCATATCAAATGCAACGTACAAAGAAATAGGGCTTCTGACCTGTGAAGCAACAGTCAATGGGCATTTGTATAAGACA
                                                                                  720
AGTAGTATAGTTTACGTTGCATGTTTCTTTATCCCGAAGACTGGACACTTCGTTGTCAGTTACCCGTAAACATATTCTGT

F   I   I   S   N   A   T   Y   K   E   I   G   L   L   T   C   E   A   T   V   N   G   H   L   Y   K   T
                                           ─── hFLT1 (domain 1-3). ─────────────────────────────────

AACACGAGAGTTCAAATGACCTGGAGTTACCCTGATGAAAAAAATAAGAGAGCTTCCGTAAGGCGACGAATTGACCAAAG
                                                                                  800
TTGTGCTCTCAAGTTTACTGGACCTCAATGGGACTACTTTTTTATTCTCTCGAAGGCATTCCGCTGCTTAACTGGTTTC

N   T   R   V   Q   M   T   W   S   Y   P   D   E   K   N   K   R   A   S   V   R   R   R   I   D   Q   S
─────────────────────────────── hFLT1 (domain 1-3). ────────────────────────

CAATTCCCATGCCAACACATATTCTACAGTGTTCTTACTATTGACAAAATGCAGAACAAAGACAAAGGACTTTATACTTGTC
                                                                                  880
GTTAAGGGTACGGTTGTGTATAAGATGTCACAAGAAGAATGATAACTGTTTTACGTCTCTTGTTTCTGTTTCCTGAAATATGAACAG

N   S   H   A   N   I   F   Y   S   V   L   T   I   D   K   M   Q   N   K   D   K   G   L   Y   T   C
                                     ─── hFLT1 (domain 1-3). ──────────────────────

GTGTAAGGAGTGGACCATCATTCAAATCTGTTAACACCTCAGTGCATATAGGAGAAATTGAAGCCATAGTCGTGCCTGTT
                                                                                  960
CACATTCCTCACCTGGTAGTTTAGACAATTGTGGAGTCACGTATATCCTCTTTAACTTCGGTATCAGCACGGACACAG

R   V   R   S   G   P   S   F   K   S   V   N   T   S   V   H   I   G   E   I   E   A   I   V   V   P   V
         ─── hFLT1 (domain 1-3). ─────                              ──── gp130 transmembrane-
```

Figure 5 (continued)

```
TGCTTAGCATTCCTATTGACAACTCTTCTGGGAGTGCTGTTCTGCTTTAATAAAAAACACATCTG
                                                                      1040
ACGAATCGTAAGGATAACTGTTGAGAAGACCCTCACGACAAGACGAATTATTCGCTCTGGATTAATTTTTGTGTAGAC
 C  L  A  F  L  L  T  L  L  G  V  L  F  C  F  N  K  R  D  L  K  K  H  I  W
                      gp130 transmembrane domain.          gp130 intracellular domain.

GCCTAATGTTCCAGATCCTTCAAAGAGTCATATTGCCCAGTGGTCACCTCACACTCCTCCAAGGCACAATTTTAATTCAA
                                                                                 1120
CGGATTACAAGGTCTAGGAAGTTTCTCAGTATAACGGGTCACCAGTGGAGTGTGAGGAGGTTCCGTGTTAAAATTAAGTT
 P  N  V  P  D  P  S  K  S  H  I  A  Q  W  S  P  H  T  P  P  R  H  N  F  N  S
                                       gp130 intracellular domain.

AAGATCAAATGTATTCAGATGGCAATTTCACTGATGTAAGTGTTGTGGAAATAGAAGCAAATGACAAAAAGCCTTTTCCA
                                                                                 1200
TTCTAGTTTACATAAGTCTACCGTTAAAGTGACTACATTCACAACACCTTTATCTTCGTTACTGTTTTCGGAAAAGGT
 K  D  Q  M  Y  S  D  G  N  F  T  D  V  S  V  V  E  I  E  A  N  D  K  K  P  F  P
                                       gp130 intracellular domain.

GAAGATCTGAAATTATTGGACCTGTTCAAAAAGGAAAAAATTAATACTGAAGGACACAGCAGTGGTATTGGGGGGTCTTC
                                                                                 1280
CTTCTAGACTTTAATAACCTGGACAAGTTTTTCCTTTTTTAATTATGACTTCCTGTGTCGTCACCATAACCCCCAGAAG
 E  D  L  K  L  L  D  L  F  K  K  E  K  I  N  T  E  G  H  S  S  G  I  G  G  S
                                       gp130 intracellular domain.
```

Figure 5 (continued)

```
ATGCATGTCATCTTTCTAGGCCAAGCATTTCTAGCAGTGATGAAAATGAATCTTCACAAAACACTTCGAGCACTGTCCAGT
                                                                                    1360
TACGTACAGTAGAAGATCCGGTTCGTAAAGATCGTCACTACTTTTACTTAGAAGTGTTTTGTGAAGCTCGTGACAGGTCA
 C   M   S   S   R   P   S   I   S   S   D   E   N   E   S   S   Q   N   T   S   S   T   V   Q
 ─────────────────────────────────────────── gp130 intracellular domain. ────────────

ATTCTACCGTGGTACACAGTGGCTACAGAGACACCAAGTTCCGTCAGTCTTCTCAAGATCCGAGTCTACCCAGCCC
                                                                                1440
TAAGATGGCACCATGTGTCACCGATGTCTGTGGTTCAAGGCAGTCAGGTTCAGAAGAGTTCTAGGCTCAGATGGGTCGGG
 Y   S   T   V   V   H   S   G   Y   R   H   Q   V   P   S   V   Q   V   F   S   R   E   S   T   Q   P
 ─────────────────────────────────────────── gp130 intracellular domain. ────────────

TTGTTAGATTCAGAGGAGGCGGCCAGAAGATCTACAATTAGTAGATCATGTAGATGGGGTGATGGTATTTTGCCCAGGCA
                                                                                    1520
AACAATCTAAGTCTCCTCCGCCGGTCTTCTAGATGTTAATCATCTAGTACATCTAGTACATCTACCGCCACTACCATAAAACGGGTCCGT
 L   L   D   S   E   E   R   P   E   D   L   Q   L   V   D   H   V   D   G   G   D   G   I   L   P   R   Q
 ─────────────────────────────────────────── gp130 intracellular domain. ────────────

ACAGTACTTCAAACAGAACTGCAGTCAGCATGAATCCAGTCCAGATATTTCACATTTTGAAAGGTCAAAGCAAGTTTCAT
                                                                                    1600
TGTCATGAAGTTTGTCTTGACGTCAGTCGTCAGTACTTAGGTCAGGTCTATAAAGTGTAAACTTTCCAGTTTCGTTCAAAGTA
 Q   Y   F   K   Q   N   C   S   Q   H   E   S   S   P   D   I   S   H   F   E   R   S   K   Q   V   S
 ─────────────────────────────────────────── gp130 intracellular domain. ────────────
```

Figure 5 (continued)

```
CAGTCAATGAGGAAGATTTTGTTAGACTTAAAACAGCAGATTTCAGATCATATTTCACAATCCTGTGGATCTGGGCAAATG
      +         +         +         +         +         +         +         +        1680
GTCAGTTACTCCTTCTAAAACAATCTGAATTTGTCGTCTAAAGTCTAGTATAAAGTGTTAGGACACCTAGACCCGTTTAC

S  V  N  E  E  D  F  V  R  L  K  Q  Q  I  S  D  H  I  S  Q  S  C  G  S  G  Q  M
                                            ─────────────────────────────────────
                                            gp130 intracellular domain.

AAAATGTTTCAGGAAGTTTCTGCAGCAGATGCCTTTTGGTCCAGGTACTGAGGGACAAGTAGAAAGATTTGAAACAGTTGG
      +         +         +         +         +         +         +         +        1760
TTTTACAAAGTCCTTCAAAGACGTCGTCTACGGAAAACCAGGTCCATGACTCCCTGTTCATCTTTCTAAACTTTGTCAACC

K  M  F  Q  E  V  S  A  A  D  A  F  G  P  G  T  E  G  Q  V  E  R  F  E  T  V  G
───────────────────────────────────────────────────────────────────────────────────
                              gp130 intracellular domain.

CATGGAGGCTGCAGACTGATGAAGGCATGCCTAAAAAGTTACTTACCACAGACTGTACGGCAAGGCGGCTACATGCCTCAGT
      +         +         +         +         +         +         +         +        1840
GTACCTCCGACGCTGACTACTTCCGTACGGATTTTCAATGAATGGTGTCTGACAGCTGTACGGAGTCA

M  E  A  A  T  D  E  G  M  P  K  S  Y  L  P  Q  T  V  R  Q  G  G  Y  M  P  Q
─────────────────────────────────────────────────────────────────────────
                       gp130 intracellular domain.

IMMUNOINTERACTIVE MOLECULES

CROSS-REFERENCE TO RELATED APPLICATIONS

This application is a continuation of U.S. application Ser. No. 10/440,295, filed May 16, 2003, now abandoned, which claims priority from U.S. Provisional Patent Application Ser. No. 60/381,285, filed on May 17, 2002.

BACKGROUND OF THE INVENTION

1. Field of the Invention

The present invention relates generally to immunointeractive molecules and more particularly antibodies which bind to vascular endothelial growth factor-B (VEGF-B) or its functional or structural equivalent and inhibit the biological activity of VEGF-B. In particular, the present invention relates to deimmunized molecules such as humanized or human antibodies that bind to VEGF-B and inhibit the biological activity of VEGF-B. These antibodies have uses in the treatment or prevention of diseases associated with perturbations in normal vasculogenesis or angiogenesis or vascular remodelling. The present invention further contemplates a method of modulating diseases associated with perturbations in normal vasculogenesis or angiogenesis or vascular remodelling by the administration of the subject antibodies. The present invention further provides an assay system useful for identifying antibodies which bind to VEGF-B and block the biological activity of VEGF-B. Accordingly, a method of screening for inhibitors of the biological activity of VEGF-B is also provided.

2. Description of the Prior Art

The reference to any prior art in this specification is not and should not be taken as an acknowledgment or any form of suggestion that the prior art forms part of the common general knowledge in any country.

Bibliographic details of the publications referred to in this specification are also collected at the end of the description.

The normal growth of new blood vessels, or physiological angiogenesis, is an essential step in vertebrate growth and development as well as in the repair of wounds and bone fractures. This process of blood vessel formation and remodelling is kept in close control by pro- and anti-angiogenic molecules, but perturbations in the process can occur. Abnormal or pathological angiogenesis occurs when the balance of blood vessel growth is disturbed and is a contributory factor in the development of a wide range of diseases, such as rheumatoid arthritis (Kasama et al., *Arthritis Rheum.* 44(11): 2512-2524, 2001) and malignant angiogenic tumours and cancer-cell metastases (Liu et al., *J. Surg. Res.* 102(1): 31-34, 2002).

Growth and remodelling of the vascular system are mediated by a diverse collection of polypeptide growth factors. One such group is the peptide family known as vascular endothelial growth factors (VEGFs) (Tuder et al., *J. Pathol.* 195(3): 367-374, 2001). The VEGFs constitute a group of structurally and functionally related growth factors that modulate many important physiological functions of endothelial cells. The mammalian members of the VEGF family identified to date include VEGF-A, VEGF-B, VEGF-C, VEGF-D and placental growth factor.

The various homologues of VEGF differ slightly in the roles they play during the various developmental stages and also in response to vascular trauma. This is indicated by the variations in temporal and spatial release of the various VEGFs during physiological events such as embryonic development, regulation of capillary growth in normal and pathological conditions in adults, and in the maintenance of the normal vasculature. For example, VEGF-A is a potent mitogen that plays a vital role in vasculogenesis and angiogenesis during development (Brown et al., *Am. J. Physiol. Lung Cell Mol. Physiol.* 281(4): L1001-1010, 2001). It is also vital for revascularization during repair of dermal wounds (Mat this et al., *Am J. Pathol* 160(1): 289-296, 2002) and regrowth of vasculature following bone fractures (Street et al., *J. Orthop. Res.* 19(6): 1057-1066, 2001).

Gene knockout experiments have found that VEGF-B is not essential for the growth and development of the peripheral vascular system, although it is involved in the normal development of the coronary vasculature (Bellomo et al., *Circ. Res.* 86(2): E29-35, 2000). It also plays a part in physiological responses to ischemia and vascular occlusion (Bellomo et al. [2000; supra]). VEGF-B is also implicated in a number of pathological angiogenic conditions such as pulmonary hypertension (Rich et al., *J. Heart Lung Transplant* 21(1): 159, 2002), the growth of angiogenic tumors (Li et al., *Growth Factors* 19(1): 49-59, 2001) and the spread or metastases of cancer cells, possibly through its effects on plasminogen activation (Gunningham et al., *J. Pathol.* 193(3): 325-332, 2001).

The actions of VEGF-B are mediated through the receptor tyrosine kinase VEGF receptor-1 (VEGF-R1). VEGF-R1 is also referred to as Flt-1 and its extracellular domain is characterized by seven immunoglobulin-like regions (Ma et al., *Biotechnol. Appl. Biochem.* 34 (Pt 3): 199-204, 2001), referred to as Ig domains 1-7.

The suspected role of VEGF-B in pathological angiogenesis has made this growth factor a desirable control point in the treatment of a number of diseases. Biological profiling of VEGF-B has, however, been limited by a lack of simple in vitro assay systems.

When further characterizing the biological effects of VEGF-B, the inventors faced difficulties with sub-optimal cell-based assays. Reports of activity of VEGF-B on endothelial cells, including stimulation of proliferation and induction of mRNA for uPA and PAI-1 have subsequently been attributed to contaminating heterodimer and lipopolysaccharide, respectively. The present inventors have now devised a novel, cellular based assay for VEGF-B activity which is based on the development of a chimeric fusion molecule encoding the extracellular portion of the VEGF-B receptor. The assay is also useful for identifying modulators of VEGF-B-Flt-1-mediated signalling.

Antibodies to VEGF-B may potentially act as antagonists of VEGF-B biological activity. In accordance with the present invention, antibodies are identified which bind to VEGF-B and block VEGF-B binding to VEGF-R1, thereby inhibiting the biological activity of VEGF-B.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention provides immunointeractive molecules such as in the form of antibodies which function as VEGF-B antagonists and may be used for treating certain conditions associated with VEGF-B activity, such as pathological angiogenesis, or other biological processes mediated by VEGF-B. The present invention also provides methods for treating these conditions comprising administering a VEGF-B antagonist to a patient afflicted with such a condition. Also provided are compositions for use in such methods which comprise one or more VEGF-B antagonists. Reference to "VEGF-B" includes polypeptides and proteins having VEGF-B-like activity. Furthermore, a VEGF-B molecule may be naturally occurring or may be a mutant, derivative, homolog or analog of VEGF-B.

The antibodies of the present invention bind, interact or otherwise associate with VEGF-B or a fragment comprising an epitope from VEGF-B. In a preferred embodiment, the antibodies bind to VEGF-B and inhibit or at least reduce the binding of VEGF-B to VEGF-R1, thereby blocking some or all the biological activity of VEGF-B.

The antibodies may be specific for VEGF-B from a particular species, such as human VEGF-B, or, in view of the level of sequence similarity between VEGF-B from different species, the antibodies may show some cross-reactivity with VEGF-B from two or more species. In the case of antibodies directed towards human VEGF-B, some level of cross-reactivity with other mammalian forms of VEGF-B may be desirable in certain circumstances, such as for example, for the purpose of testing antibodies in animal models of a particular disease and for conducting toxicology studies in a manner where VEGF-B signaling in the test animal is affected by the test antibody. Species where cross-reactivity of an antibody to human VEGF-B may be desirable include a non-human primate such as monkey, gorilla, orangutan or marmoset, sheep, cow, goat, pig, donkey, horse, dog, cat, rat, mouse and guinea pig. Accordingly, one preferred group of antibodies are those which exhibit some level of species cross-reactivity. A particularly preferred group of such antibodies are those to human VEGF-B which exhibit some level of species cross-reactivity.

Antibodies of the present invention include, but are not limited to antibodies which bind VEGF-B and inhibit VEGF-B induced signaling through VEGF-R1.

Preferably, the antibodies are monoclonal antibodies or antigen-binding fragments thereof. Most preferably, the antibodies are deimmunized, humanized or human antibodies suitable for administration to humans. These include humanized antibodies prepared, for example, from murine monoclonal antibodies and human monoclonal antibodies which may be prepared, for example, using transgenic mice or by phage display.

Antibodies in accordance with the present invention include the murine monoclonal antibodies 2H10, B33/02-1C6-6, B33/02-2F5-2 and 36/01-4E12-11-12 and humanized forms thereof.

The present invention contemplates methods of modulating VEGF-B-mediated diseases or conditions by the administration of antibodies of the present invention. Conditions to be treated in accordance with the present invention include pulmonary hypertension, the growth of angiogenic tumors and the spread or metastases of cancer cells, chronic inflammatory diseases such as rheumatoid arthritis and any other VEGF-B-mediated diseases or conditions where there is known to be a significant angiogenic component.

The present invention also provides an assay system useful for identifying antibodies that inhibit the biological activity of VEGF-B. Accordingly, a method of screening for inhibitors of VEGF-B biological activity, which method involves the assay system, is provided.

A summary of sequence identifiers used throughout the subject specification is provided in Table 1.

TABLE 1

Summary of sequence identifiers

| SEQUENCE ID NO: | DESCRIPTION |
|---|---|
| 1 | Nucleotide sequence encoding VEGF-R1-(Hflt1-4)gp130 fusion |
| 2 | Corresponding amino acid sequence of VEGF-R1-(hflt1-4)gp130 fusion |
| 3 | Nucleotide sequence encoding VEGF-R1-(hflt1-3)gp130 fusion |
| 4 | Corresponding amino acid sequence of VEGF-R1(hflt1-4)-gp130 fusion |
| 5-11 | oligonucleotides |

BRIEF DESCRIPTION OF THE FIGURES

FIG. 4 is a representation of the complete nucleotide and amino acid sequences (SEQ ID NOS: 3-4) of human FLT1-3 gp130 (VEGF-R1), including the sequences representing IL-3 signal, FLAG tag, hFLT1 (domains 1-3), gp130 including gp130 transmembrane domain and gp130 intracellular domain.

FIG. 5 is a representation of the complete nucleotide and amino acid sequences (SEQ ID NOS: 1-2) of human Flt1-4 gp130 hgp130TM (VEGF-R1), including the sequences representing IL-3 signal, FLAG tag, hFLT1 (domains 1-4), gp130 including gp130 transmembrane domain and gp130 intracellular domain.

Figure 6:
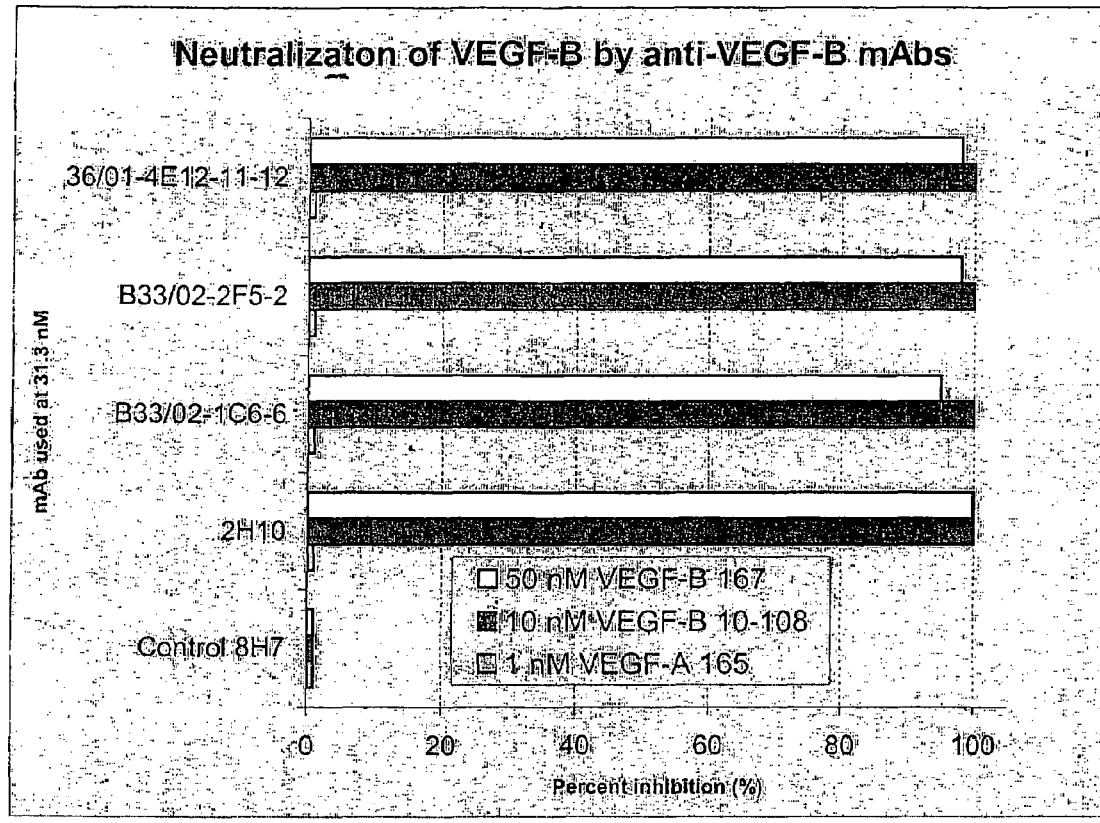

FIG. 6 shows that the VEGF-B specific mAbs 36/01-4E12-11-12, B33/02-2F5-2, B33/02-1C6-6 and 2H10 inhibit the cellular response to VEGF-B isoforms 167 and 10-108 but not VEGF-A. Ba/F3 cells transfected with chimeric VEGF-R1/EpoR were stimulated with VEGF-$_{B167}$ (50 nM), VEGF-$_{B10-108}$ (10 nM) or VEGF-A (1 nM) in the presence of test or control mAb (8H7) at a constant concentration of 31.3 nM. Cell viability was assessed at 72 hours. The VEGF-B specific mAbs neutralized the biological activity of VEGF-$B_{167}$ and VEGF-$B_{10-108}$ but as expected had no effect on the biological activity of VEGF-A. The control mAb 8H7 had no neutralising effect on the biological activity of VEGF-$B_{167}$, VEGF-$B_{10-108}$ and VEGF-A.

DETAILED DESCRIPTION OF THE INVENTION

Before describing the present invention detail, it is to be understood that unless otherwise indicated, the subject invention is not limited to specific formulation components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to a "an antibody" includes a single compound, as well as two or more antibodies; reference to "VEGF-B" includes a single VEGF-B, as well as two or more VEGF-B molecules; and so forth.

In describing and claiming the present invention, the following terminology will be used in accordance with the definitions set forth below.

The terms "antibody", "immunointeractive molecule", "active agent", "pharmacologically active agent", "medicament", "active" and "drug" are used interchangeably herein to refer to a chemical compound that induces a desired pharmacological, physiological effect such as antagonizing VEGF-R1-mediated signaling. The terms also encompass pharmaceutically acceptable and pharmacologically active ingredients of those active agents specifically mentioned herein including but not limited to salts, esters, amides, prodrugs, active metabolites, analogs and the like. When the terms "antibody", "immunointeractive molecule", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

By the terms "effective amount" or "therapeutically effective amount" of an antibody, agent and the like as used herein are meant a sufficient amount of the antibody to provide the desired therapeutic effect including antagonism between VEGF-B and VEGF-R1. Of course, undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration, the condition to be treated and the like. Thus, it may not be possible to specify an exact "effective amount". However, an appropriate "effective amount" in any individual case may be determined by one of ordinary skill in the art using only routine experimentation.

By "pharmaceutically acceptable" carrier excipient or diluent is meant a pharmaceutical vehicle comprised of a material that is not biologically or otherwise undesirable, i.e. the material may be administered to a subject along with the selected antibody without causing any or a substantial adverse reaction. Carriers may include excipients and other additives such as diluents, detergents, coloring agents, wetting or emusifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of a condition or disorder. Thus, for example, "treating" a patient involves prevention of a particular disorder or adverse physiological event in a susceptible individual as well as treatment of a clinically symptomatic individual by inhibiting or causing regression of a disorder or disease. Thus, for example, the present method of "treating" a patient in need of therapy of the vascular system encompasses both prevention of a condition, disease or disorder as well as treating the condition, disease or disorder. In any event, the present invention contemplates the treatment or prophylaxis of vascular-type disease conditions and disorders. Such diseases, disorders and defects include pulmonary hypertension, the growth of angiogenic tumors and the spread or metastases of cancer cells, chronic inflammatory diseases such as rheumatoid arthritis and any other VEGF-B-mediated diseases or conditions where there is known to be a significant angiogenic component.

"Patient" as used herein refers to a mammalian, preferably human, individual who can benefit from the pharmaceutical formulations and methods of the present invention. There is no limitation on the type of mammal that could benefit from the presently described pharmaceutical formulations and methods. A patient regardless of whether a human or non-human mammal may be referred to as an individual, subject, mammal, host or recipient.

The preferred animals to be treated are humans or other primates, livestock animals, laboratory test animals, companion animals or captured wild animals.

The present invention relates generally to immunointeractive molecules which bind, interact or otherwise associated to or with VEGF-B or a fragment, portion or part thereof and inhibit or otherwise reduce the biological activity of VEGF-B and which may be employed in the methods of the present invention. An immunointeractive molecule includes antibodies and derivatives, fragments and recombinant or modified forms thereof including Fv, Fab, Fab', F(ab')$_2$, single chain antibodies and Fc fragments. The preferred antibodies are monoclonal antibodies or antigen-binding fragments thereof. Preferably, the antibodies are in isolated, homogenous or fully or partially purified form.

An antibody may be a chimeric antibody including a fusion of antibody portions or molecules.

Most preferably, the antibodies are deimmunized, humanized or human antibodies suitable for administration to humans. These include deimmunized or humanized antibodies prepared, for example, from murine monoclonal antibodies, and human monoclonal antibodies which may be prepared, for example, using transgenic mice as described below, or by phage display.

Reference to "VEGF-B" is reference to the protein and its encoding nucleotide sequence described in the literature as VEGF-related factor or VEGF-B (Grimmond et al., *Genome Res.* 6(2): 122-129, 1996; Townson et al., *Biochem. Biophys. Res. Commun.* 220(3): 922-928, 1996), and in International Patent Publication Nos. WO 96/26736 and WO 96/27007.

Reference to "binding" of an antibody means binding, interacting or associating with or to a target antigen such as VEGF-B. Reference to "VEGF-B" includes fragments or portions which comprise the epitopes to which an antibody binds. Consequently, reference to an antibody binding to VEGF-B includes the binding, interaction or association of the antibody or an antigen-binding portion thereof, to VEGF-B or a part, fragment or epitope-containing region thereof. A "VEGF-B" protein includes a polypeptide or protein having VEGF-B-like properties including an ability to interact with VEGF-R1.

Generally, "binding", "interaction" or "association" means or includes the specific binding, interaction or association of the antibody to VEGF-B or a portion thereof.

The biological effects of VEGF-B are mediated by VEGF-R1.

The present invention is hereinafter described with reference to antibodies and VEGF-B. This is done, however, with the understanding that other immunointeractive molecules may be used and antibodies may be directed to polypeptides having at least one biological property in common with VEGF-B. Furthermore, in terms of animal studies, rather than humanized antibodies, mammalianized or other deimmunized antibodies may be employed for use in non-human primates or laboratory test mammals.

Examples of antibodies contemplated by the present invention include those that bind to VEGF-B and inhibit or otherwise reduce the biological activity of VEGF-B. Such antibodies, referred to herein as blocking or neutralising antibodies, may be raised with VEGF-B or immunogenic parts thereof and screened in assays for the ability to block the signaling of VEGF-B through VEGF-R1. Suitable assays are assays that test the antibodies for the ability to inhibit the binding of VEGF-B to cells expressing VEGF-R1, or that test antibodies for the ability to reduce a biological or cellular response that results from the signaling of VEGF-B through VEGF-R1.

In one embodiment, the present invention provides antibodies that bind to VEGF-B and inhibit or otherwise reduce the biological activity of VEGF-B.

Preferably the antibodies are monoclonal antibodies or antigen-binding fragments thereof.

Most preferably, the antibodies are deimmunized, humanized or human monoclonal antibodies suitable for use in human therapeutics.

As such, in a preferred embodiment, the present invention provides antibodies that are deimmunized, humanized or human monoclonal antibodies which bind to VEGF-B and inhibit or otherwise reduce VEGF-B signaling through VEGF-R1 or a hybrid-type receptor.

In an especially preferred embodiment, the present invention provides antibodies that are deimmunized, humanized or human monoclonal antibodies which bind to VEGF-B and inhibit the biological activity of VEGF-B.

Reference to an "antibody" or "antibodies" includes reference to all the various forms of antibodies, including but not limited to whole antibodies, antibody fragments, including, for example, Fv, Fab, Fab' and F(ab')$_2$ fragments, humanized antibodies, human antibodies (e.g., produced in transgenic animals or through phage display) and immunoglobulin-derived polypeptides produced through genetic engineering techniques. An Fc portion from these antibodies is also contemplated even if this does not have any binding specificity.

Unless stated otherwise, specificity in respect of an antibody of the present invention is intended to mean that the antibody does not exhibit any meaningful cross-reactivity with non-VEGF-B proteins. However, it is not intended to indicate that there is no cross-reactivity with other forms of VEGF-B which may exist, (for example, splice variants or fragments of VEGF-B), nor is it intended to indicate that no cross-reactivity with VEGF-B from other species may exist. The amino acid sequence of VEGF-B is a well conserved across species, with other mammalian forms of the receptor showing high levels of amino acid homology with the human VEGF-B chain. For example, the human and mouse VEGF-B$_{10-108}$ protein has 91.9% identity over the 99 amino acids, the human and mouse VEGF-B$_{167}$ protein has 88.0% identity over the 167 amino acids and the human and mouse VEGF-B$_{186}$ protein has 87.1% identity over the 186 amino acids. Reference to "identity" generally means after optimal alignment.

The antibodies may be specific for VEGF-B from a particular species, such as human VEGF-B, or, because of the level sequence similarity between VEGF-B from certain mammalian species, may show some cross-reactivity with VEGF-B from other mammalian species. In the case of antibodies directed towards human VEGF-B, some level of cross reactivity with other mammalian forms of VEGF-B may be desirable in certain circumstances. For example, such antibodies are useful for the purpose of testing antibodies in animal models of a particular disease, and for conducting toxicology studies in a manner where VEGF-B signaling in the test animal is affected by the test antibody. Species where cross reactivity of an antibody to human VEGF-B may be desirable include primates such as monkeys, orangutans, marmosets and gorillas, livestock animals such as sheep, cattle, horses, goats, donkeys, pigs, laboratory test animals such as mice, rats, guinea pigs, hamsters and companion animals such as dog and rat. Accordingly, one preferred group of antibodies are those which exhibit some level of species cross reactivity. A particularly preferred group of antibodies are those antibodies to human VEGF-B which exhibit some level of species cross-reactivity.

In a preferred embodiment, the present invention provides antibodies that bind to human VEGF-B and to cynomolgus monkey VEGF-B and inhibit the biological activity of VEGF-B.

In a further preferred embodiment, the present invention provides antibodies that bind to human VEGF-B and to ovine VEGF-B and inhibit the biological activity of VEGF-B.

In still a further preferred embodiment, the present invention provides antibodies that bind to human VEGF-B and to canine VEGF-B and inhibit the biological activity of VEGF-B.

In yet a further preferred embodiment, the present invention provides antibodies that bind to human VEGF-B and to rat VEGF-B and inhibit the biological activity of VEGF-B.

In yet a further preferred embodiment, the present invention provides antibodies that bind to human VEGF-B and to murine VEGF-B and inhibit the biological activity of VEGF-B.

The antibodies of the present invention may be prepared by well known procedures. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

One method for producing an antibody of the present invention comprises immunizing a non-human animal, such as a mouse or a transgenic mouse, with a VEGF-B polypeptide, or immunogenic parts thereof whereby antibodies directed against the VEGF-B polypeptide are generated in said animal.

Both polyclonal and monoclonal antibodies can be produced by this method. The methods for obtaining both types of sera are well known in the art. Polyclonal sera are less preferred but are relatively easily prepared by injection of a suitable laboratory animal with an effective amount of an VEGF-B polypeptide, or immunogenic parts thereof, collecting serum from the animal and isolating VEGF-B specific sera by any of the known immunoadsorbent techniques. Antibodies produced by this technique are generally less favoured, because of the potential for heterogeneity of the product.

The use of monoclonal antibodies is particularly preferred because of the ability to produce them in large quantities and the homogeneity of the product. Monoclonal antibodies may be produced by conventional procedures.

The present invention contemplates a method for producing a hybridoma cell line comprises immunizing a non-human animal, such as a mouse or a transgenic mouse, with an VEGF-B polypeptide, or immunogenic parts thereof; harvesting spleen cells from the immunized animal; fusing the harvested spleen cells to a myeloma cell line to generate hybridoma cells; and identifying a hybridoma cell line that produces a monoclonal antibody that binds a VEGF-B polypeptide.

Such hybridoma cell lines and the anti-VEGF-B monoclonal antibodies produced by them are encompassed by the present invention. Monoclonal antibodies secreted by the hybridoma cell lines are purified by conventional techniques. Hybridomas or the monoclonal antibodies produced by them may be screened further to identify monoclonal antibodies with particularly desirable properties, such as the ability to inhibit the biological activity of VEGF-B.

The VEGF-B polypeptide or immunogenic part thereof that may be used to immunize animals in the initial stages of the production of the antibodies of the present invention may be from any mammalian source. Preferably, the VEGF-B polypeptide or immunogenic part thereof is human VEGF-B.

Antigen-binding fragments of antibodies of the present invention may be produced by conventional techniques. Examples of such fragments include, but are not limited to, Fab, Fab', F(ab')2 and Fv fragments, including single chain Fv fragments (termed sFv or scFv).

Antibody fragments and derivatives produced by genetic engineering techniques, such as disulphide stabilized Fv fragments (dsFv), single chain variable region domain (Abs) molecules and minibodies are also contemplated for use. Unless otherwise specified, the terms "antibody" and "monoclonal antibody" as used herein encompass both whole antibodies and antigen-binding fragments thereof.

Such derivatives of monoclonal antibodies directed against VEGF-B may be prepared and screened for desired properties, by known techniques, including the assays described herein. The assays described herein provide the means to identify derivatives of the antibodies of the present invention that bind to VEGF-B and inhibit the biological activity of VEGF-B. Certain of the techniques involve isolating DNA encoding a polypeptide chain (or a portion thereof) of a mAb of interest, and manipulating the DNA through recombinant DNA technology. The DNA may be fused to another DNA of interest, or altered (e.g. by mutagenesis or other conventional techniques) to add, delete, or substitute one or more amino acid residues, for example.

DNA encoding antibody polypeptides (e.g. heavy or light chain, variable region only or full length) may be isolated from B-cells of mice that have been immunized with VEGF-B. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Single chain antibodies may be formed by linking heavy and light chain variable region (Fv region) fragments via an amino acid bridge (short peptide linker), resulting in a single polypeptide chain. Such single-chain Fvs (scFvs) have been prepared by fusing DNA encoding a peptide linker between DNAs encoding the two variable region polypeptides (VL and VH). The resulting antibody fragments can form dimers or trimers, depending on the length of a flexible linker between the two variable domains (Kortt et al., *Protein Engineering* 10: 423, 1997). Techniques developed for the production of single chain antibodies include those described in U.S. Pat. No. 4,946,778; Bird (*Science* 242: 423, 1988), Huston et al. (*Proc. Natl. Acad. Sci. USA* 85: 5879, 1988) and Ward et al. (*Nature* 334: 544, 1989). Single chain antibodies derived from antibodies provided herein are encompassed by the present invention.

In one embodiment, the present invention provides derivatives of the antibodies of the present invention that bind to VEGF-B and inhibit the biological activity of VEGF-B.

Techniques are known for deriving an antibody of a different subclass or isotype from an antibody of interest, i.e., subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g. DNA encoding the constant region of an antibody of the desired isotype.

The monoclonal production process described above may be used in animals, for example mice, to produce monoclonal antibodies. Conventional antibodies derived from such animals, for example murine antibodies, are known to be generally unsuitable for administration to humans as they may cause an immune response. Therefore, such antibodies may need to be subjected to a humanization process in order to provide antibodies suitable for administration to humans. Such humanization processes are well known in the art and are described in further detail below.

Additional embodiments include chimeric antibodies and humanized versions of murine monoclonal antibodies. Such chimeric or humanized antibodies may be prepared by known techniques, for example, CDR grafting, and offer the advantage of reduced immunogenicity when the antibodies are administered to humans. In one embodiment, a chimeric monoclonal antibody comprises the variable region of a murine antibody (or just the antigen binding site thereof) and a constant region derived from a human antibody. Alternatively, a humanized antibody fragment may comprise the antigen binding sites (complementarity determining regions CDRs) of a murine monoclonal antibody and a variable region fragment (lacking the antigen-binding site) derived from a human antibody. Procedures for the production of chimeric and humanized monoclonal antibodies include those described in Riechmann et al. (*Nature* 332: 323, 1988) Liu et al. (*Proc. Natl. Acad. Sci. USA* 84: 3439, 1987), Larrick et al. (*Bio/Technology* 7: 934, 1989) and Winter and Harris (*TIPS* 14: 139, 1993).

The complementarity determining regions (CDRs) of a given antibody may be identified using the system described by Kabat et al. in Sequences of Proteins of Immunological Interest, 5th Ed., U.S. Department of Health and Human Services, PHS, NIH, NIH Publication No. 91-3242, 1991).

For example, the murine monoclonal antibody 2H10 may be subjected to humanization to reduce the immunogenicity of the antibody in a target host. Murine monoclonal antibody 2H10 has a specific and potent antagonistic effect against VEGF-B and inhibits the biological activity of VEGF-B. However, the potential immunogenicity of mAb 2H10 in other hosts, and in particular humans, makes the use of mAb 2H10 unsuitable as a therapeutic agent in these hosts. The murine monoclonal antibodies B33/02-1C6-6, B33/02-2F5-2 and 36/01-4E12-11-12 may also be subjected to humanization. The present invention, however, extends to any deimmunized, humanized or human monoclonal antibodies directed to VEGF-B.

In a particular embodiment contemplated by the present invention, the antibodies of the present invention comprise within the variable region of their light chain, at least one of the CDRs found in the light chain of mAb 2H10. Thus, among the antibodies contemplated by the present invention are those that comprise from one to all three of the CDR sequences from the light chain variable region of mAb 2H10. Further, among the antibodies contemplated by the present invention are those that comprise from one to all three of the CDR sequences from the heavy chain variable region of mAb 2H10. In a preferred embodiment, among the antibodies contemplated by the present invention are those that comprise from one to all six CDR sequences from the heavy and light chain variable regions of mAb 2H10. In further embodiments contemplated by the present invention, the antibodies of the present invention comprise within the variable region of their light chain one or more CDRs found in the light chain of monoclonal antibodies B33/02-1C6-6 or B33/02-2F5-2 or 36/01-4E12-11-12.

Procedures for generating human antibodies in non-human animals have also been developed and are well known to those skilled in the art. The antibodies may be partially human, or preferably completely human. For example, transgenic mice into which genetic material encoding one or more human immunoglobulin chains has been introduced may be used to produce the antibodies of the present invention. Such mice may be genetically altered in a variety of ways. The genetic manipulation may result in human immunoglobulin polypeptide chains replacing endogenous immunoglobulin chains in at least some (preferably virtually all) antibodies produced by the animal upon immunization.

Mice in which one or more endogenous immunoglobulin genes have been inactivated by various means have been prepared. Human immunoglobulin genes have been introduced into the mice to replace the inactivated mouse genes. Antibodies produced in the animals incorporate 22 human immunoglobulin polypeptide chains encoded by the human genetic material introduced into the animal. Examples of techniques for production and use of such transgenic animals are described in U.S. Pat. Nos. 5,814,318, 5,569,825, and 5,545,806, which are incorporated by reference herein.

As such, antibodies of the present invention may include, but are not limited to, partially human (preferably fully human) monoclonal antibodies that inhibit the biological activity of VEGF-B.

Another method for generating human antibodies is phage display. Phage display techniques for generating human antibodies are well known to those skilled in the art, and include the methods used by companies such as Cambridge Antibody Technology and MorphoSys and which are described in International Patent Publication Nos. WO 92/01047, WO 92/20791, WO 93/06213 and WO 93/11236.

Antibodies of the present invention may be employed in vitro or in vivo. Among the uses for antibodies of the present invention are assays (either in vitro or in vivo) to detect the presence of VEGF-B polypeptides and immunoaffinity chromatography to purify VEGF-B polypeptides. Further, those antibodies of the present invention that can inhibit the biological activity of VEGF-B may be used to inhibit a biological activity that results from VEGF-B signalling through the VEGF-R1 receptor.

Therefore, in one embodiment, such antibodies may be used in therapeutic applications to treat disorders caused or exacerbated (directly or indirectly) by the signaling of VEGF-B through the VEGF-R1 receptor. A therapeutic application involves in vivo administration of a blocking antibody to a mammal in an amount effective to inhibit signaling by VEGF-B through the VEGF-R1 receptor. Preferably, the antibodies are human or humanized monoclonal antibodies of the present invention.

The antibodies may be used to treat diseases or conditions induced by VEGF-B, including but not limited to pulmonary hypertension, the growth of angiogenic tumors and the spread or metastases of cancer cells, chronic inflammatory diseases such as rheumatoid arthritis and any other VEGF-B-mediated diseases or conditions where there is known to be a significant angiogenic component.

Antibodies in accordance with the present invention include the murine monoclonal antibodies 2H10, B33/02-1C6-6, B33/02-2F5-2 and 36/01-4E12-11-12 and humanized forms thereof.

Particular monoclonal antibodies of the invention are selected from the group consisting of mAb 2H10; a mAb that is cross-reactive with mAb 2H10; a mAb that binds to the same epitope as mAb 2H10; a mAb that competes with mAb 2H10 for binding to VEGF-B; a mAb that possesses a biological activity of mAb 2H10; and an antigen-binding fragment of any of the foregoing antibodies.

In one embodiment, the antibody has a binding affinity for human VEGF-B that is substantially equivalent to the binding affinity of mAb 2H10 for human VEGF-B. mAb 2H10 is an IgG2a antibody. mAbs of other isotypes (including but not limited to IgG4), derived from mAb 2H10 are also encompassed by the present invention. Hybridoma cell lines that produce any such monoclonal antibodies also are provided by the present invention.

Procedures for switching (altering) the subclass or isotype of an antibody are also well known to those skilled in the art. Such procedures may involve, for example, recombinant DNA technology, whereby DNA encoding antibody polypeptide chains that confer the desired subclass is substituted for DNA encoding the corresponding polypeptide chain of the parent antibody. This procedure is useful, for example, in certain antibody therapeutic applications where are particular antibody isotype is preferred, such as in the treatment of asthma where IgG4 may be the preferred antibody isotype.

One example of a biological activity of mAb 2H10 is the ability to bind to VEGF-B and inhibit the biological activity of VEGF-B. In one embodiment, a mAb of the invention possesses VEGF-B biological activity blocking activity substantially equivalent to that of mAb 2H10.

The ability of the antibodies of the present invention to inhibit the biological activity of VEGF-B can be confirmed in a number of assays.

One assay that may be used for identifying antibodies which function as VEGF-B antagonists and inhibit the biological activity of VEGF-B is described below and in the Examples.

In this assay, 293A12-cells are engineered to express chimeric polypeptides comprising the extracellular domain of either VEGF-R1 operably connected to the transmembrane and cytoplasmic domains of the protein, gp130. When the engineered 293A12-cells are in the presence of VEGF-B the chimeric polypeptides form a homodimeric receptor complex which permits signal transduction to occur. The VEGF-B-mediated signal transduction is observable via an identifiable signal, such as the activation of a gene encoding a reporter molecule (Example 5).

Anti-VEGF-B antibodies that antagonize VEGF-B signaling through the VEGF-R1 receptor will inhibit VEGF-B-mediated activation of the reporter molecule.

The level of signal transduction is conveniently determined by selecting cells wherein signal transduction activates a pathway regulating the expression of a gene encoding a reporter molecule that provides an identifiable signal. Preferred reporter molecules are enzymes such as luciferase.

293A12 cells are particularly preferred in this assay as they are 293T cells which stably express genetic material encoding a luciferase reporter molecule (Example 1). The expression of the luciferase reporter molecule is regulated by a STAT-3 signaling pathway which is activated by gp130 signaling.

The signal transduction portion from gp130 is particularly preferred, as it induces STAT-3 phosphorylation which leads to the expression of the STAT-3 activated luciferase reporter gene. However, the signal transduction portion from other molecules may also be employed. The choice of the signal transduction portion of the polypeptides must be matched to the activation or promoter portion of the gene encoding the reporter molecule.

Those skilled in the art appreciate that the cell based assays of the invention, for example described above and in Example 4, may be utilised as a basis for screening for modulators of VEGF-B/VEGF-R1 interaction. While such methods are well known to those skilled in the art, a brief description of the method is provided herein. The method involves subjecting appropriately engineered cells to a signal producing amount of VEGF-B under conditions where, in the absence of any antagonism of ligand receptor binding, a signal, for example luciferase expression, may be detected. The exposure is then conducted in the presence of test compounds and the level of signal detected compared with that detected in the absence of a test compound. Test compounds may include compound libraries, for example libraries of natural product extracts or libraries of synthetic compounds. Alternatively, phage display libraries of antibody variable domains and the like, or panels of monoclonal antibodies against VEGF-B may be screened across the assay.

Chimeric polypeptides that may be used in the assay of the present invention are described in Example 1 and comprise the amino acid sequences set forth in SEQ ID NO:2 and SEQ ID NO:4.

cDNA encoding the chimeric polypeptides contemplated for use in this assay comprise a nucleotide sequence selected from SEQ ID NO: 1 and SEQ ID NO: 3. The sequence defined by SEQ ID NO: 1 comprises a sequence which encodes the extracellular immunoglobulin (Ig) domains (D) 1 to 4 of human VEGF-R1 fused to the transmembrane and cytoplasmic domains of gp130. SEQ ID NO: 3 comprises a sequence which encodes the extracellular immunoglobulin (Ig) domains (D) 1 to 3 of human VEGF-R1 fused to the transmembrane and cytoplasmic domains of gp130.

Although 293A12 cells are described in the assay of the present invention, other cells may be used. Generally a eukaryotic cell is employed, and more particularly, a mammalian cell. The mammalian cells may be derived from humans, livestock animals, laboratory test animals and companion animals. Non-mammalian cells contemplated herein include cells from avian species, reptilian species, amphibian species and insect species.

The term "operably connected" is used in its broadest context to include molecules which have associated together such that they are in functional interaction with each other. Generally, the association is by a chemical linkage or bond. Preferably, the chemical linkage or bond is a peptide bond. The terms include, therefore, a polypeptide comprising a contiguous series of amino acids each linked via a peptide bond wherein one contiguous series of amino acids has ligand-binding properties and another contiguous series of amino acids has signal transduction properties.

Pharmaceutically acceptable carriers and/or diluents include any and all solvents, dispersion media, coatings, antibacterial and antifungal agents, agents used for adjusting tonicity, buffers, chelating agents, and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin. The compositions may also include buffers and chelating agents.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

The amount of active compound in such therapeutically useful compositions is such that a suitable dosage will be obtained.

The compositions of the present invention are useful in modifying a VEGF-B-mediated condition including but not limited to pulmonary hypertension, the growth of angiogenic tumors and the spread or metastases of cancer cells, chronic inflammatory diseases such as rheumatoid arthritis and any other VEGF-B-mediated diseases or conditions where there is known to be a significant angiogenic component.

The human and humanized antibodies of the present invention are useful in the treatment of such conditions. Any adverse condition resulting from VEGF-B interaction with VEGF-R1 may be treated or prevented by the administration of the human and humanised monoclonal antibodies of the present invention.

Accordingly, another aspect of the present invention contemplates a method for the treatment or prophylaxis of a condition mediated by VEGF-B such as but not limited to a chronic inflammatory condition, said method comprising administering to a subject an effective amount of a deimmunized, humanized or human monoclonal antibody of the present invention for a time and under conditions sufficient to inhibit the biological activity of VEGF-B.

An "effective amount" in this context is an amount of an antibody sufficient to reduce VEGF-B signaling through the VEGF-R1 receptor by at least 40%, preferably at least 50%, more preferably by at least 60%, still more preferably by at least 70-80% or greater than 90%. For example, the reduction in signal may be by at least 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%. Reduction in signaling may be measured in any number of ways including inhibition or antagonism of binding between VEGF-B and VEGF-41 or reduction in activity of VEGF-R1 fused to a receptor molecule.

The method may also be measured at the level of amelioration of symptoms. Hence, an effective amount would be that amount required to at least partially alleviate symptoms of, for example, inflammation.

Preferably, the subject is a human. However, veterinary applications are also contemplated for livestock animals as well as companion animals. In such cases it would be necessary to prepare an appropriate antibody designed to avoid an immunogenic response to the antibody by the mammal.

In a specific embodiment, the present invention contemplates a method for ameliorating the effects of VEGF-B mediated conditions in a human subject, said method comprising administering to said subject an effective amount of a humanized monoclonal antibody of the present invention or its equivalent for a time and under conditions sufficient to ameliorate the effects of inflammation.

The present invention further contemplates the use of a humanized monoclonal antibody of the present invention or its equivalent in the manufacture of a medicament in the treatment or prophylaxis of an inflammatory condition in a subject.

The present invention is further described by the following non-limiting Examples.

EXAMPLE 1

Development of Assays for Analysis of VEGF-B-Receptor Interaction

Endothelial cells do not proliferate in response to VEGF-R1 ligands and no simple, biological assay system for the measurement of VEGF-B activity has been described.

The present inventors reasoned that an assay system that would provide a more reliable and quantifiable response to ligand-induced receptor activation would facilitate the analysis of the biological activities of VEGF-B.

Mammalian Cell Culture and Transfection

Human 293T cells were transfected using Lipofectamine 2000 according to the manufacturer's instructions. Cells co-transfected with plasmids encoding either puromycin resistance or hygromycin resistance were subsequently selected and maintained in media supplemented with puromycin (25 μg/ml) or hygromycin (60 μg/ml) respectively. 293A12 cells were derived from 293T cells following stable transfection with a luciferase reporter under the control of a STAT-3 promoter (Nicholson et al., *Proc. Natl. Acad. Sci. USA* 97: 6493-6498, 2000). When stimulated with cytokines that activate STAT-3 such as leukaemia inhibitory factor (LIF) and interleukin-6 (IL-6), luciferase expression 10-15 fold in excess of background is induced within 24 hours.

Clone 2.1.19.25 was derived from 293A12 cells following stable transfection with a chimeric receptor construct (see below). For assay of VEGF-R1 ligand activity 2.1.19.25 cells were plated into 96 well ViewPlates (Packard Bioscience, Australia) at $5 \times 10^4$/well and ligands added to the indicated concentration to give a final assay volume of 100 μl. Luciferase was assessed at 18-24 hours (LucLite Kit, Packard Bioscience, Australia).

Expression, Purification and Refolding of VEGF-B Isoforms

The VEGF-B isoforms, VEGF-$B_{167}$ and VEGF-$B_{186}$, and a truncated form, VEGF-$B_{10-108}$, are expressed in *E. coli* as N-terminal $His_6$-tagged proteins.

Recombinant VEGF-$B_{167}$ is expressed in *E. coli* using the pET15b vector with downstream purification and refolding as previously described (Scrofani et al., *Protein Science* 9: 2018-2025, 2000).

The coding region of mature human VEGF-$B_{10-108}$ protein is amplified using PCR [95° C. for 2 minutes, 1 cycle; 94° C. for 1 minute, 60° C. for 1 minute, 72° C. for 1 minute—30 cycles; 72° C. for 1 minute—1 cycle; 1.5 U Expand High Fidelity PCT System enzyme mix to introduce in frame BamHI HindIII restriction enzyme sites, at the 5' and 3' ends respectively, using the oligonucleotides:

```
5'Oligo:                                  [SEQ ID NO:5]
5'-CACGGATCCGCAGCACACTATCACCAGAGGAAAG-3'

3'Oligo:                                  [SEQ ID NO:6]
3'-GCATAAGCTTTCACTTTTTTTTAGGTCTGCATTC-3'
```

The resulting PCR-derived DNA fragment is digested with BamHI and HindIII and ligated into BamHI and HindIII digested pQE30 (QIAGEN, Germany). The VEGF-$B_{10-108}$-pQE30 is transformed into M15[pREP4] *E. coli* (QIAGEN) using an electroporator according to the manufacturer's instructions. The VEGF-$B_{10-108}$ protein displays an additional 16 amino acids at the N-terminus which incorporate a $His_6$ tag and a Genenase I cleavage site. The VEGF-$B_{10-108}$ protein is isolated from *E. coli* inclusion bodies and purified and refolded as previously described (Scrofani et al., 2000, supra).

The coding region of mature human VEGF-$B_{186}$ is amplified by PCR and cloned into pET15b. In contrast to the other isoforms, VEGF-$B_{186}$ is purified directly from whole *E. coli* cell lysate rather than inclusion bodies. Pelleted cells are suspended in a buffer of 6 M guanidine hydrochloride (GdCl), 0.1 M $NaH_2PO_4$, 10 mM Tric-HCl, 10 mM 2-mercaptoethanol, 0.02% w/v Tween-20, pH 8.0 at 10 mL per gram of cells and incubated overnight at 37° C. The solution is centrifuged and the supernatant is decanted and filtered. Nickel affinity chromatography and further downstream purification and refolding are performed as previously described (Scrofani et al., 2000, supra).

Figure 1:
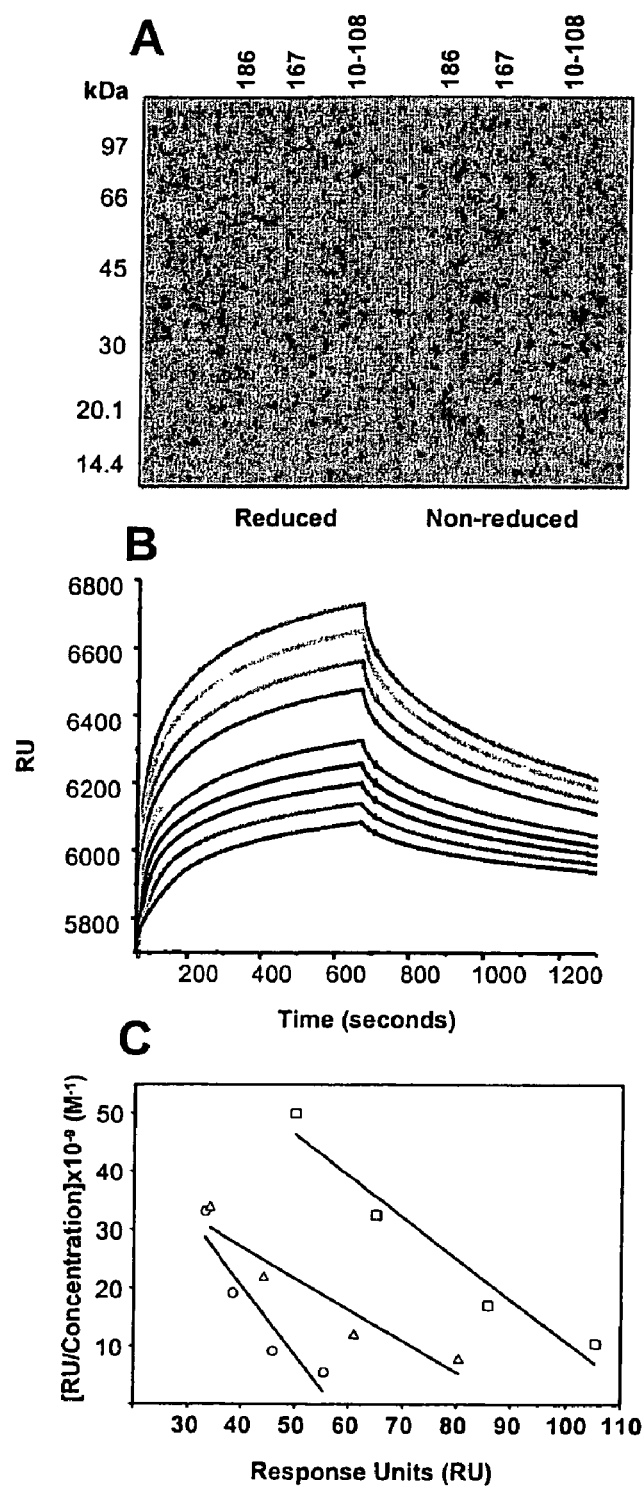
FIG. 1 shows the biochemical analysis of recombinant VEGF-B isoforms. (A) VEGF-B isoforms expressed in *E. coli* were purified and refolded then analyzed by SDS-PAGE (10-20% gradient) under reducing and non-reducing conditions. The gel was stained with Coomassie blue. (B) Representative example of Biosensor dose-response analysis of VEGF-B$_{186}$ binding to VEGF-R1$_{D2}$. Concentration range 0.1 nM to 500 nM. C. Scatchard analysis of VEGF-B$_{167}$ (□), VEGF-B$_{186}$ (Δ) and VEGF-B$_{10-108}$ (○) binding to VEGF-R1$_{D2}$. KDs were determined as 1.5 nM for VEGF-B$_{167}$, 2.0 nM for VEGF-B$_{186}$ and 0.8 nM for VEGF-B$_{10-108}$.

Metal affinity chromatography under reducing and denaturing conditions was used to purify monomeric VEGF-B proteins and, following dialysis refolding, dimeric protein is separated from monomeric and high molecular weight multimeric forms using a combination of reverse-phase HPLC and hydrophilic chromatography. SDS-PAGE analysis of the three, refolded VEGF-B proteins is shown (FIG. 1).

Development of a Cell-Based Assay

Figure 2:
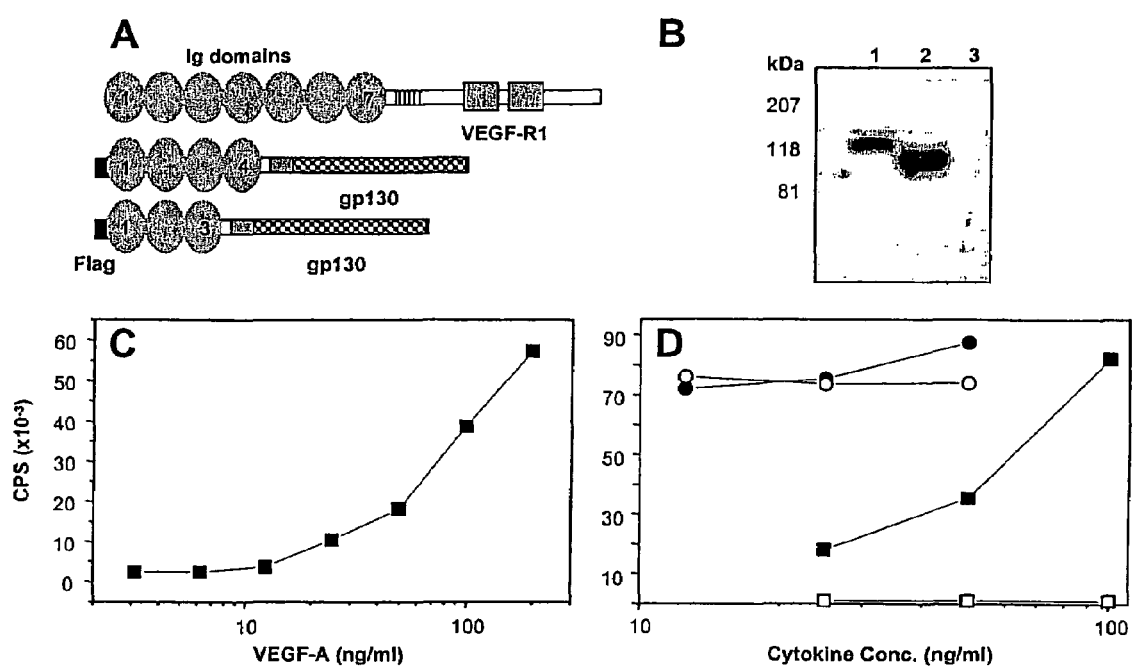
FIG. 2 shows the aspects of the novel biological assay for VEGF-R1 ligands. (A) Schematic representation of VEGF-R1 and chimeric receptors incorporating VEGF-R1$_{D1-4}$ or R1$_{D1-3}$ and the transmembrane and intracellular domains of gp130. (B) Chimeric receptors cloned into pEFBOS-S-Flag for expression as N-terminal Flag-tagged proteins were transiently expressed in 293T cells. Cell lysates were subjected to SDS-PAGE, transferred to a nylon membrane and probed using an anti-Flag antibody (lane 1, chimeric R1$_{D1-4}$; lane 2, chimeric R1$_{D1-3}$; lane 3, control plasmid). (C) Clone 2.1.19.25 was derived following stable transfection of 293A12 cells with the chimeric receptor construct incorporating VEGF-R1$_{D1-4}$. (D) VEGF-A antagonist (VEGF-R1$_{D1-4}$-IgGFc chimeric protein, R&D Systems) inhibits the 2.1.19.25 luciferase response to VEGF-A but not to LIF (VEGF-A [■]; VEGF-A plus antagonist [□]; LIF [●]; LIF plus antagonist [○]).

The present inventors used splice-overlap extension PCR to generate a series of chimeric receptors and developed an assay-based on a chimeric receptor strategy. The strategy involves joining the extracellular immunoglobulin (Ig) domains of VEGF-R1 (preferably D1 to D4 or D1 to D3) to the cytoplasmic domains of gp130 (gp130 transmembrane domain—amino acids 574 to 595 and gp130 cytoplasmic domain—amino acids 595 to 918) (FIG. 2).

Using VEGF-R1 and gp130 cDNAs as templates, a human VEGF-R1-gp130 chimeric receptor cDNA is generated by splice-overlap-extension PCR. Briefly, the coding region of extracellular immunoglobulin (Ig) domains (D) 1 to 4 and 1 to 3 of human VEGF-R1 are amplified by PCR [96° C. for 2 mins, 1 cycle; 94° C. for 30 seconds, 55° C. for 30 seconds, 68° C. for 1.5 minutes—35 cycles; 1.5 U Expand High Fidelity PCT System enzyme mix (Roche Diagnostics, Mannheim, Germany) using the oligonucleotides:

```
5'Oligo                                    [SEQ ID NO:7]
5'-ATATGGCGCGCCTAGTCAGCTACTGGGACACCGGGGTC-3'

3'Oligo (domains 1 to 4):                  [SEQ ID NO:8]
5'-CAGGCACGACTATGGCTTCAATTTCTCCGGCCTTTTCGTAAATCTGG
GTTTTCAC-3'

3'Oligo (domains 1 to 3):                  [SEQ ID NO:9]
5'-CACGACTATGGCTTCAATTTCTCCTATATGCACTGAGGTGTTAACAG
ATTTG-3'
```

Similar PCR conditions are used to amplify the human gp130 transmembrane and cytoplasmic domains using the following oligonucleotides:

```
5'Oligo:                                   [SEQ ID NO:10]
5'-ACGTACGCGTTCACTGAGGCATGTAGCCGCCTTGCCG-3

3'Oligo:                                   [SEQ ID NO:11]
5'-GGAGAAATTGAAGCCATAGTCGTGCCTGTTTGCTTAGC-3'
```

To generate chimeric cDNA the PCR products are mixed and a further PCR using the same conditions with the 5' sense VEGF-R1 oligonucleotide and the 3'antisense gp130 oligonucleotide are performed. This PCR product is designed to incorporate 5' Asc1 site and 3' Mlu1 restriction enzyme sites and after digestion of the PCR product with these enzymes, the chimeric cDNA is ligated into an Mlu1 digested mammalian expression vector, pEFBOS-S-FLAG (Nicholson et al., 2000, supra) for expression as an N-terminal FLAG-tagged protein.

Details of both chimeric receptors are provided in schematic form in FIG. 2. Transient expression in 293T cells, followed by Western blot analysis with anti-FLAG antibodies confirmed that the constructs encode a protein of the expected molecular weight (FIG. 2B).

For assay development, the chimeric receptor construct incorporating VEGF-R1 D1 to D4 and a vector incorporating a hygromycin resistance gene were co-transfected into 293A12 cells. Following hygromycin selection, isolated resistant colonies were picked and expanded, then assayed for luciferase after incubation in the presence of VEGF-A. Eleven of the 63 colonies assayed expressed luciferase in response to VEGF-A and colony 2.1.19 was subsequently cloned by limit dilution. Dose-response analysis of clone 2.1.19.25 to VEGF-A is shown in FIG. 2C. In further analysis, this response was shown to be completely inhibited by soluble VEGF-R1-IgG-Fc chimeric receptor protein (R&D Systems, UK; FIG. 2D). As expected the VEGF-R1-IgG-Fc chimeric protein did not inhibit 2.1.19.25 luciferase production in response to LIF. Over a large number of assays the VEGF-A signal to background ratio have varied between 2.5 to 3.

Figure 3A:
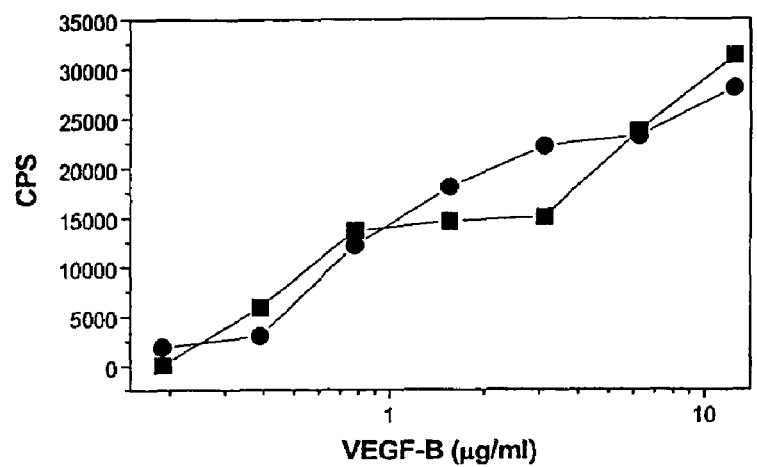
FIG. 3 shows an assay of VEGF-B biological activity and characterization of VEGF-B specific mAbs. (A). Clone 2.1.19.25 response to VEGF-B$_{167}$ (●) and VEGF-B$_{10-108}$ (■). (B). Monoclonal Ab 2H10 inhibits the 2.1.19.25 response to VEGF-B$_{167}$. 2.19.25E cells were incubated with titrating VEGF-B$_{167}$ alone (■) or supplemented with VEGF-B specific mAb 2H10 (●) or 7C3 (▲) or control (▼) at a final concentration of 50 µg/ml.

The refolded VEGF-B isoforms were assessed for biological activity in the 2.1.19.25 cell-based assay. Both VEGF-$B_{167}$ and VEGF-$B_{10-108}$ were shown to be active (FIG. 3A). The $ED_{50}$ for both isoforms of VEGF-B is routinely in the order of 150-300 ng/ml. VEGF-$B_{186}$ preparations have not shown activity despite display of an interaction with VEGF-R1 in Biosensor-based analysis.

The VEGF family members retain a complex secondary structure making the refolding of these proteins difficult. However, recently there has been considerable success in refolding these proteins from insoluble inclusion bodies (reviewed in Scrofani and Nash, *J. Microbiol. Biotechnol.* 11(4): 543-511, 2001). The inventors have previously described a protocol for production of dimeric VEGF-$B_{167}$ based on *E. coli* fermentation, inclusion body isolation and dialysis refolding. In the present invention, they have applied a similar strategy to express, purify and refold the other naturally occurring isoform and a truncated form of the protein that retains the core cystine-knot motif. All three proteins were purified as homodimers and demonstrated to interact with the minimal ligand binding domain of VEGF-R1.

Although the Biosensor analysis indicates appropriate folding within each monomeric subunit, it does not confirm correct inter-chain disulphide bond formation to yield a biologically active dimer. To date, the biological assay of VEGF-R1 ligand activity has been based on relatively complex readouts such as monocyte migration, smooth muscle cell MMP production and osteoclast function (Clauss et al., *J. Biol. Chem.* 271: 17269-17634, 1996; Wang and Keiser, *Circ. Res.* 83: 832-840, 1998; Niida et al., *J. Exp. Med.* 190: 293-298, 1999). The simple chimeric receptor-based assay of the present invention utilizes a reporter gene readout and is used to demonstrate the activity of VEGF-$B_{167}$ and VEGF-$B_{10-108}$. Surprisingly, the inventors did not detect activity of refolded VEGF-$B_{186}$. One explanation may be inappropriate dimerization as noted above, however, Makinen et al. (*J. Biol. Chem.* 274: 21217-21222, 1999), have reported that VEGF-$B_{186}$ expressed in mammalian cells is processed at the C-terminus and it is only after this processing occurs that it is able to interact with neuropilin-1. It is possible that the full-length C-terminal domain retained in the E. coli expressed protein may interfere with receptor dimerization and signalling.

In addition to allowing demonstration of recombinant protein biological activity, the new cell-based assay has facilitated the identification of VEGF-B antagonists, such as specific neutralizing mAbs that inhibit VEGF-B signalling mediated through VEGF-R1.

Development of a Molecular Assay

A molecular assay based on the interaction of VEGF-R1 with VEGF-B represents the best primary screen for both monoclonal antibodies and, potentially, small molecule antagonists.

The coding region of Ig domain 2 (D2) of the human VEGF-R1 protein (residues 129-229) was amplified by PCR and ligated into pQE30 vector (QIAGEN). VEGF-R1$_{D2}$ protein was isolated from E. coli inclusion bodies using a previously described protocol (Weismann et al., Cell 91: 695-704, 1997) and further purified under denaturing conditions by RP-HPLC (QIAGEN).

For initial Biosensor analysis of the binding of the purified and refolded VEGF-B isoforms, surface plasmon resonance (Biosensor 2000; Biacore, Sweden) and recombinant VEGF-R1$_{D2}$ are used. D2 has previously been demonstrated to represent the minimal ligand binding domain of VEGF-R1 (Weismann et al., 1997, supra). The three forms of VEGF-B were immobilized on separate channels of a CM5 sensor chip, while murine LIF was immobilized to a fourth channel to serve as a negative control. Interaction with VEGF-R1$_{D2}$ was monitored on all channels simultaneously.

The target molecule is immobilized to a CM5 dextran chip using amine-coupling chemistry according to the manufacturer's instructions. Briefly, 35 μL NHS/EDC (1:1) was injected onto the sensor chip at a flow rate of 5 μL/min to activate the sensor surface. Test and negative control (LIF) proteins were resuspended in 20 mM sodium acetate, pH 4.5 (final concentration 7-20 μg/mL) and injected directly onto the sensor surface. Post coupling, 50 mM diaminoethane, pH 9.0 was used to quench residual activated sites on the biosensor surface. Two cycles of 0.1 M phosphoric acid (30 μL; 50 μL/min) were performed at the end of each run to regenerate the sensor chip surface.

Purified VEGF-R1$_{D2}$ is diluted to varying concentrations in 0.1% w/v BSA, 20 mM HEPES, 0.15 M NaCl, 0.005% w/v Tween 20, 3.4 mM EDTA, pH 7.4. Receptor binding is simultaneously monitored on VEGF-B$_{10-108}$, VEGF-B$_{167}$, VEGF-B$_{186}$ and mLIF control channel at a flow rate of 5 μL/min. Scatchard analysis is used to determine binding kinetics at steady state equilibrium.

A dose-response analysis of human VEGF-R1$_{D2}$ binding is completed. The molecules VEGF$_{10-108}$, VEGF-B$_{167}$ and VEGF-B$_{186}$ clearly associate with VEGF-R1$_{D2}$ with similar kinetics (FIGS. 2B and 2C). The truncated VEGF-B10-108 appears to have a slightly higher affinity for VEGF-R1$_{D2}$ (KD=0.8 nM) than exhibited by either VEGF-B$_{176}$ (KD 1.5 nN) or VEGF-B$_{186}$ (KD 2.0 nM).

EXAMPLE 2

Analysis of VEGF-B-Specific Neutralizing mAbs Using New Assays

Analysis Using Biochemical Assays-Biosensor and ELISA

Monoclonal antibodies which bind to and inhibit the biological activity of VEGF-B (neutralizing antibodies) would represent valuable tools for characterization of VEGF-B function and may be used to generate valuable therapeutic agents through the process of mouse antibody humanisation.

Figure 3B:
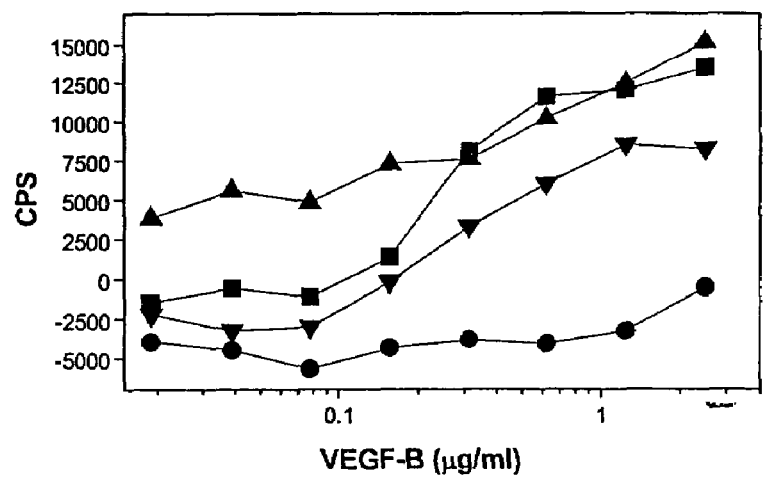

A panel of mAbs is raised against the VEGF-B$_{167}$ isoform and are screened for VEGF-B antagonist activity in the cell-based assay described above. The results are presented in FIG. 3. The mAb 2H10 but not the VEGF-B specific mAb 7C3 or control unrelated mAb 6A9 was able to inhibit VEGF-B binding activity in the entire test range. mAb 2H10 is unable to block the cellular responses to VEGF-A.

ELISA-based analysis is performed and reveals that mAb 2H10 binds to both of the naturally occurring isoforms of VEGF-B, VEGF-B$_{167}$ and VEGF-B$_{186}$ as well as the short 10-108 form used for structural studies. Western blot analysis shows that this monoclonal antibody reacts only with these proteins under non-denaturing conditions, suggesting that 2H10 targets the core receptor-binding domain of VEGF-B and, as a consequence, the mAb is anticipated to inhibit the activity of all VEGF-B isoforms.

In addition to 2H10, the anti-VEGF-B mAbs B33/02-1C6-6, B33/02-2F5-2 and 36/01-4E12-11-12 have been identified as antagonists of VEGF-B biological activity (see FIG. 6). Antagonist activity was characterised using a cell viability assay similar to the cell-based assay described in Example 1 above. The cell viability assay used a murine IL-3-dependant pro-B cell line, Ba/F3, transfected to stably express chimeric VEGFR-1 extracellular domains with the cytoplasmic domain of the erythropoietin receptor (VEGFR-1/EpoR). These cells, in addition to proliferating in response to IL-3, will also proliferate in response to cytokines that signal through VEGF-R1 such as VEGF-A and VEGF-B. Cell viability was estimated colourmetrically by the enzymatic reduction of a tetrazolium dye 3-(4,5-dimethylthiazol-2-yl)-5-(3-carboxymethoxyphenyl)-2-(4-sulfophenyl)-2H-tetrazolium (MTS) and phenylmetha-sulfazone (PMS).

The hybridoma that produces monoclonal antibody 2H10 was deposited on Jul. 27, 2005 with American Type Culture Collection (ATCC), 10801 University Blvd., Manassas, Va. 20110-2209, U.S.A., under Accession No.PTA-6889.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Altschul et al., Nucl. Acids Res. 25: 3389. 1997

Ausubel et al., "Current Protocols in Molecular Biology" John Wiley & Sons Inc, 1992 Chapter 15

Ausubel et al., "Current Protocols in Molecular Biology" John Wiley & Sons Inc, 1994-1998, Beaucage and Carruthers, Tetra. Letts. 22: 1859-1862, 1981

Bellomo et al, Circ. Res. 86(2): E29-35, 2000

Bonner and Laskey Eur. J. Biochem. 46: 83, 1974

Brown et al., Am. J. Physiol Lung Cell Mol. Physiol. 281(4): L1001-1010, 2001

Clauss et al., J. Biol. Chem. 271: 17269-17634, 1996

Douillard and Hoffman, "Basic Facts about Hybridomas", in Compendium of Immunology Vol. II, ed. Schwartz, 1981

Fiers et al., Nature 273: 113-120, 1978

Grimmond et al., Genome Res. 6(2): 12-129, 1996

Gunningham et al., J. Pathol. 193(3): 325-332, 2001

Jakoby and Pastan (eds), *Cell Culture. Methods in Enzymology*, Vol. 58, 1979 (Academic Press, Inc., Harbour Brace Jovanovich, New York
Johnson et al., *J. Virol.* 66: 2952-2965, 1993
Kasama et al., *Arthritis Rheum.* 44(11): 2512-2524, 2001
Kohler and Milstein, *European Journal of Immunology* 6: 511-519, 1976
Kohler and Milstein, *Nature* 256: 495-499, 1975
Kubo et al., *FEBS Lett.* 241: 119, 1988
Kyte and Doolittle, *J. Mol. Biol.* 157: 105-132, 1982
Li et al., *Growth Factors* 19(1): 49-59, 2001
Liu et al., *J. Surg. Res.* 102(1): 31-34, 2002
Ma et al., *Biotechnol. Appl. Biochem.* 34: (Pt 3): 199-204, 2001
Makinen et al., *J. Biol. Chem.* 274: 21217-21222, 1999
Marmur and Doty *J. Mol. Biol.* 5: 109, 1962
Matteucci et al., *J. Am. Chem. Soc.* 103: 3185, 1981
Matthis et al., *Am. J. Pathol.* 160(1): 289-296, 2002
Nicholson et al., *PNAS* 97: 6493-6498, 2000
Niida et al., *J. Exp. Med.* 190: 293-298, 1999
Rich et al., *J. Heart Lung Transplant* 21(1): 159, 2002
Sambrook et al., Molecular Cloning: A Laboratory Manual, 2nd Ed., Cold Spring Harbor Laboratory, Cold Spring Harbor, N.Y., 1989
Scrofani and Nash, 2001
Scrofani et al., *Protein Science* 9: 2018-2025, 2000
Street et al., *J. Orthop. Res.* 19(6): 1057-1066, 2001
Townson et al., *Biochem. Biphys. Res. Commun.* 220(3): 922-928, 1996
Tuder et al., *J Pathol.* 195(3): 367-374, 2001
Wang and Keiser, *Circ. Res.* 83: 832-840, 1998
Weismann et al., *Cell* 91: 695-704, 1997

SEQUENCE LISTING

```
<160> NUMBER OF SEQ ID NOS: 11

<210> SEQ ID NO 1
<211> LENGTH: 2277
<212> TYPE: DNA
<213> ORGANISM: human
<220> FEATURE:
<221> NAME/KEY: CDS
<222> LOCATION: (1)..(2277)
<223> OTHER INFORMATION:

<400> SEQUENCE: 1 atg gtt ctt gcc agc tct acc acc agc atc cac acc atg ctg ctc ctg        48
Met Val Leu Ala Ser Ser Thr Thr Ser Ile His Thr Met Leu Leu Leu
1               5                   10                  15 ctc ctg atg ctc ttc cac ctg gga ctc caa gct tca atc tcg gcg cgc        96
Leu Leu Met Leu Phe His Leu Gly Leu Gln Ala Ser Ile Ser Ala Arg
                20                  25                  30 cag gac tac aag gac gac gat gac aag acg cgc cag tct agt tca ggt       144
Gln Asp Tyr Lys Asp Asp Asp Asp Lys Thr Arg Gln Ser Ser Ser Gly
            35                  40                  45 tca aaa tta aaa gat cct gaa ctg agt tta aaa ggc acc cag cac atc       192
Ser Lys Leu Lys Asp Pro Glu Leu Ser Leu Lys Gly Thr Gln His Ile
        50                  55                  60 atg caa gca ggc cag aca ctg cat ctc caa tgc agg ggg gaa gca gcc       240
Met Gln Ala Gly Gln Thr Leu His Leu Gln Cys Arg Gly Glu Ala Ala
65                  70                  75                  80 cat aaa tgg tct ttg cct gaa atg gtg agt aag gaa agc gaa agg ctg       288
His Lys Trp Ser Leu Pro Glu Met Val Ser Lys Glu Ser Glu Arg Leu
                85                  90                  95 agc ata act aaa tct gcc tgt gga aga aat ggc aaa caa ttc tgc agt       336
Ser Ile Thr Lys Ser Ala Cys Gly Arg Asn Gly Lys Gln Phe Cys Ser
                100                 105                 110 act tta acc ttg aac aca gct caa gca aac cac act ggc ttc tac agc       384
Thr Leu Thr Leu Asn Thr Ala Gln Ala Asn His Thr Gly Phe Tyr Ser
            115                 120                 125 tgc aaa tat cta gct gta cct act tca aag aag aag gaa aca gaa tct       432
Cys Lys Tyr Leu Ala Val Pro Thr Ser Lys Lys Lys Glu Thr Glu Ser
        130                 135                 140 gca atc tat ata ttt att agt gat aca ggt aga cct ttc gta gag atg       480
Ala Ile Tyr Ile Phe Ile Ser Asp Thr Gly Arg Pro Phe Val Glu Met
145                 150                 155                 160 tac agt gaa atc ccc gaa att ata cac atg act gaa gga agg gag ctc       528
Tyr Ser Glu Ile Pro Glu Ile Ile His Met Thr Glu Gly Arg Glu Leu
```

-continued

|  | 165 | 170 | 175 |  |
|---|---|---|---|---|
| gtc att ccc tgc cgg gtt acg tca cct aac atc act gtt act tta aaa<br>Val Ile Pro Cys Arg Val Thr Ser Pro Asn Ile Thr Val Thr Leu Lys<br>180 185 190 | | | | 576 |
| aag ttt cca ctt gac act ttg atc cct gat gga aaa cgc ata atc tgg<br>Lys Phe Pro Leu Asp Thr Leu Ile Pro Asp Gly Lys Arg Ile Ile Trp<br>195 200 205 | | | | 624 |
| gac agt aga aag ggc ttc atc ata tca aat gca acg tac aaa gaa ata<br>Asp Ser Arg Lys Gly Phe Ile Ile Ser Asn Ala Thr Tyr Lys Glu Ile<br>210 215 220 | | | | 672 |
| ggg ctt ctg acc tgt gaa gca aca gtc aat ggg cat ttg tat aag aca<br>Gly Leu Leu Thr Cys Glu Ala Thr Val Asn Gly His Leu Tyr Lys Thr<br>225 230 235 240 | | | | 720 |
| aac tat ctc aca cat cga caa acc aat aca atc ata gat gtc caa ata<br>Asn Tyr Leu Thr His Arg Gln Thr Asn Thr Ile Ile Asp Val Gln Ile<br>245 250 255 | | | | 768 |
| agc aca cca cgc cca gtc aaa tta ctt aga ggc cat act ctt gtc ctc<br>Ser Thr Pro Arg Pro Val Lys Leu Leu Arg Gly His Thr Leu Val Leu<br>260 265 270 | | | | 816 |
| aat tgt act gct acc act ccc ttg aac acg aga gtt caa atg acc tgg<br>Asn Cys Thr Ala Thr Thr Pro Leu Asn Thr Arg Val Gln Met Thr Trp<br>275 280 285 | | | | 864 |
| agt tac cct gat gaa aaa aat aag aga gct tcc gta agg cga cga att<br>Ser Tyr Pro Asp Glu Lys Asn Lys Arg Ala Ser Val Arg Arg Arg Ile<br>290 295 300 | | | | 912 |
| gac caa agc aat tcc cat gcc aac ata ttc tac agt gtt ctt act att<br>Asp Gln Ser Asn Ser His Ala Asn Ile Phe Tyr Ser Val Leu Thr Ile<br>305 310 315 320 | | | | 960 |
| gac aaa atg cag aac aaa gac aaa gga ctt tat act tgt cgt gta agg<br>Asp Lys Met Gln Asn Lys Asp Lys Gly Leu Tyr Thr Cys Arg Val Arg<br>325 330 335 | | | | 1008 |
| agt gga cca tca ttc aaa tct gtt aac acc tca gtg cat ata tat gat<br>Ser Gly Pro Ser Phe Lys Ser Val Asn Thr Ser Val His Ile Tyr Asp<br>340 345 350 | | | | 1056 |
| aaa gca ttc atc act gtg aaa cat cga aaa cag cag gtg ctt gaa acc<br>Lys Ala Phe Ile Thr Val Lys His Arg Lys Gln Gln Val Leu Glu Thr<br>355 360 365 | | | | 1104 |
| gta gct ggc aag cgg tct tac cgg ctc tct atg aaa gtg aag gca ttt<br>Val Ala Gly Lys Arg Ser Tyr Arg Leu Ser Met Lys Val Lys Ala Phe<br>370 375 380 | | | | 1152 |
| ccc tcg ccg gaa gtt gta tgg tta aaa gat ggg tta cct gcg act gag<br>Pro Ser Pro Glu Val Val Trp Leu Lys Asp Gly Leu Pro Ala Thr Glu<br>385 390 395 400 | | | | 1200 |
| aaa tct gct cgc tat ttg act cgt ggc tac tcg tta att atc aag gac<br>Lys Ser Ala Arg Tyr Leu Thr Arg Gly Tyr Ser Leu Ile Ile Lys Asp<br>405 410 415 | | | | 1248 |
| gta act gaa gag gat gca ggg aat tat aca atc ttg ctg agc ata aaa<br>Val Thr Glu Glu Asp Ala Gly Asn Tyr Thr Ile Leu Leu Ser Ile Lys<br>420 425 430 | | | | 1296 |
| cag tca aat gtg ttt aaa aac ctc act gcc act cta att gtc aat gtg<br>Gln Ser Asn Val Phe Lys Asn Leu Thr Ala Thr Leu Ile Val Asn Val<br>435 440 445 | | | | 1344 |
| aaa ccc cag att tac gaa aag gga gaa att gaa gcc ata gtc gtg cct<br>Lys Pro Gln Ile Tyr Glu Lys Gly Glu Ile Glu Ala Ile Val Val Pro<br>450 455 460 | | | | 1392 |
| gtt tgc tta gca ttc cta ttg aca act ctt ctg gga gtg ctg ttc tgc<br>Val Cys Leu Ala Phe Leu Leu Thr Thr Leu Leu Gly Val Leu Phe Cys<br>465 470 475 480 | | | | 1440 |
| ttt aat aag cga gac cta att aaa aaa cac atc tgg cct aat gtt cca | | | | 1488 |

```
                Phe Asn Lys Arg Asp Leu Ile Lys Lys His Ile Trp Pro Asn Val Pro
                            485                 490                 495 gat cct tca aag agt cat att gcc cag tgg tca cct cac act cct cca         1536
Asp Pro Ser Lys Ser His Ile Ala Gln Trp Ser Pro His Thr Pro Pro
        500                 505                 510 agg cac aat ttt aat tca aaa gat caa atg tat tca gat ggc aat ttc         1584
Arg His Asn Phe Asn Ser Lys Asp Gln Met Tyr Ser Asp Gly Asn Phe
            515                 520                 525 act gat gta agt gtt gtg gaa ata gaa gca aat gac aaa aag cct ttt         1632
Thr Asp Val Ser Val Val Glu Ile Glu Ala Asn Asp Lys Lys Pro Phe
    530                 535                 540 cca gaa gat ctg aaa tta ttg gac ctg ttc aaa aag gaa aaa att aat         1680
Pro Glu Asp Leu Lys Leu Leu Asp Leu Phe Lys Lys Glu Lys Ile Asn
545                 550                 555                 560 act gaa gga cac agc agt ggt att ggg ggg tct tca tgc atg tca tct         1728
Thr Glu Gly His Ser Ser Gly Ile Gly Gly Ser Ser Cys Met Ser Ser
                565                 570                 575 tct agg cca agc att tct agc agt gat gaa aat gaa tct tca caa aac         1776
Ser Arg Pro Ser Ile Ser Ser Ser Asp Glu Asn Glu Ser Ser Gln Asn
            580                 585                 590 act tcg agc act gtc cag tat tct acc gtg gta cac agt ggc tac aga         1824
Thr Ser Ser Thr Val Gln Tyr Ser Thr Val Val His Ser Gly Tyr Arg
        595                 600                 605 cac caa gtt ccg tca gtc caa gtc ttc tca aga tcc gag tct acc cag         1872
His Gln Val Pro Ser Val Gln Val Phe Ser Arg Ser Glu Ser Thr Gln
610                 615                 620 ccc ttg tta gat tca gag gag cgg cca gaa gat cta caa tta gta gat         1920
Pro Leu Leu Asp Ser Glu Glu Arg Pro Glu Asp Leu Gln Leu Val Asp
625                 630                 635                 640 cat gta gat ggc ggt gat ggt att ttg ccc agg caa cag tac ttc aaa         1968
His Val Asp Gly Gly Asp Gly Ile Leu Pro Arg Gln Gln Tyr Phe Lys
                645                 650                 655 cag aac tgc agt cag cat gaa tcc agt cca gat att tca cat ttt gaa         2016
Gln Asn Cys Ser Gln His Glu Ser Ser Pro Asp Ile Ser His Phe Glu
            660                 665                 670 agg tca aag caa gtt tca tca gtc aat gag gaa gat ttt gtt aga ctt         2064
Arg Ser Lys Gln Val Ser Ser Val Asn Glu Glu Asp Phe Val Arg Leu
        675                 680                 685 aaa cag cag att tca gat cat att tca caa tcc tgt gga tct ggg caa         2112
Lys Gln Gln Ile Ser Asp His Ile Ser Gln Ser Cys Gly Ser Gly Gln
690                 695                 700 atg aaa atg ttt cag gaa gtt tct gca gca gat gct ttt ggt cca ggt         2160
Met Lys Met Phe Gln Glu Val Ser Ala Ala Asp Ala Phe Gly Pro Gly
705                 710                 715                 720 act gag gga caa gta gaa aga ttt gaa aca gtt ggc atg gag gct gcg         2208
Thr Glu Gly Gln Val Glu Arg Phe Glu Thr Val Gly Met Glu Ala Ala
                725                 730                 735 act gat gaa ggc atg cct aaa agt tac tta cca cag act gta cgg caa         2256
Thr Asp Glu Gly Met Pro Lys Ser Tyr Leu Pro Gln Thr Val Arg Gln
            740                 745                 750 ggc ggc tac atg cct cag tga                                             2277
Gly Gly Tyr Met Pro Gln
        755

<210> SEQ ID NO 2
<211> LENGTH: 758
<212> TYPE: PRT
<213> ORGANISM: human

<400> SEQUENCE: 2
```

-continued

```
Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
            20                  25                  30

Gln Asp Tyr Lys Asp Asp Asp Lys Thr Arg Gln Ser Ser Ser Gly
        35              40                  45

Ser Lys Leu Lys Asp Pro Glu Leu Ser Leu Lys Gly Thr Gln His Ile
    50                  55                  60

Met Gln Ala Gly Gln Thr Leu His Leu Gln Cys Arg Gly Glu Ala Ala
65                  70                  75                  80

His Lys Trp Ser Leu Pro Glu Met Val Ser Lys Glu Ser Glu Arg Leu
                85                  90                  95

Ser Ile Thr Lys Ser Ala Cys Gly Arg Asn Gly Lys Gln Phe Cys Ser
            100                 105                 110

Thr Leu Thr Leu Asn Thr Ala Gln Ala Asn His Thr Gly Phe Tyr Ser
        115                 120                 125

Cys Lys Tyr Leu Ala Val Pro Thr Ser Lys Lys Lys Glu Thr Glu Ser
    130                 135                 140

Ala Ile Tyr Ile Phe Ile Ser Asp Thr Gly Arg Pro Phe Val Glu Met
145                 150                 155                 160

Tyr Ser Glu Ile Pro Glu Ile Ile His Met Thr Glu Gly Arg Glu Leu
                165                 170                 175

Val Ile Pro Cys Arg Val Thr Ser Pro Asn Ile Thr Val Thr Leu Lys
            180                 185                 190

Lys Phe Pro Leu Asp Thr Leu Ile Pro Asp Gly Lys Arg Ile Ile Trp
        195                 200                 205

Asp Ser Arg Lys Gly Phe Ile Ile Ser Asn Ala Thr Tyr Lys Glu Ile
    210                 215                 220

Gly Leu Leu Thr Cys Glu Ala Thr Val Asn Gly His Leu Tyr Lys Thr
225                 230                 235                 240

Asn Tyr Leu Thr His Arg Gln Thr Asn Thr Ile Ile Asp Val Gln Ile
                245                 250                 255

Ser Thr Pro Arg Pro Val Lys Leu Leu Arg Gly His Thr Leu Val Leu
            260                 265                 270

Asn Cys Thr Ala Thr Thr Pro Leu Asn Thr Arg Val Gln Met Thr Trp
        275                 280                 285

Ser Tyr Pro Asp Glu Lys Asn Lys Arg Ala Ser Val Arg Arg Arg Ile
    290                 295                 300

Asp Gln Ser Asn Ser His Ala Asn Ile Phe Tyr Ser Val Leu Thr Ile
305                 310                 315                 320

Asp Lys Met Gln Asn Lys Asp Lys Gly Leu Tyr Thr Cys Arg Val Arg
                325                 330                 335

Ser Gly Pro Ser Phe Lys Ser Val Asn Thr Ser Val His Ile Tyr Asp
            340                 345                 350

Lys Ala Phe Ile Thr Val Lys His Arg Lys Gln Gln Val Leu Glu Thr
        355                 360                 365

Val Ala Gly Lys Arg Ser Tyr Arg Leu Ser Met Lys Val Lys Ala Phe
370                 375                 380

Pro Ser Pro Glu Val Val Trp Leu Lys Asp Gly Leu Pro Ala Thr Glu
385                 390                 395                 400

Lys Ser Ala Arg Tyr Leu Thr Arg Gly Tyr Ser Leu Ile Ile Lys Asp
                405                 410                 415

Val Thr Glu Glu Asp Ala Gly Asn Tyr Thr Ile Leu Leu Ser Ile Lys
```

```
                     420                 425                 430
Gln Ser Asn Val Phe Lys Asn Leu Thr Ala Thr Leu Ile Val Asn Val
        435                 440                 445

Lys Pro Gln Ile Tyr Glu Lys Gly Glu Ile Glu Ala Ile Val Val Pro
    450                 455                 460

Val Cys Leu Ala Phe Leu Leu Thr Thr Leu Leu Gly Val Leu Phe Cys
465                 470                 475                 480

Phe Asn Lys Arg Asp Leu Ile Lys Lys His Ile Trp Pro Asn Val Pro
                485                 490                 495

Asp Pro Ser Lys Ser His Ile Ala Gln Trp Ser Pro His Thr Pro Pro
            500                 505                 510

Arg His Asn Phe Asn Ser Lys Asp Gln Met Tyr Ser Asp Gly Asn Phe
        515                 520                 525

Thr Asp Val Ser Val Val Glu Ile Glu Ala Asn Asp Lys Lys Pro Phe
    530                 535                 540

Pro Glu Asp Leu Lys Leu Leu Asp Leu Phe Lys Lys Glu Lys Ile Asn
545                 550                 555                 560

Thr Glu Gly His Ser Ser Gly Ile Gly Gly Ser Ser Cys Met Ser Ser
                565                 570                 575

Ser Arg Pro Ser Ile Ser Ser Ser Asp Glu Asn Glu Ser Ser Gln Asn
            580                 585                 590

Thr Ser Ser Thr Val Gln Tyr Ser Thr Val Val His Ser Gly Tyr Arg
    595                 600                 605

His Gln Val Pro Ser Val Gln Val Phe Ser Arg Ser Glu Ser Thr Gln
610                 615                 620

Pro Leu Leu Asp Ser Glu Glu Arg Pro Glu Asp Leu Gln Leu Val Asp
625                 630                 635                 640

His Val Asp Gly Gly Asp Gly Ile Leu Pro Arg Gln Gln Tyr Phe Lys
                645                 650                 655

Gln Asn Cys Ser Gln His Glu Ser Ser Pro Asp Ile Ser His Phe Glu
            660                 665                 670

Arg Ser Lys Gln Val Ser Ser Val Asn Glu Glu Asp Phe Val Arg Leu
    675                 680                 685

Lys Gln Gln Ile Ser Asp His Ile Ser Gln Ser Cys Gly Ser Gly Gln
690                 695                 700

Met Lys Met Phe Gln Glu Val Ser Ala Ala Asp Ala Phe Gly Pro Gly
705                 710                 715                 720

Thr Glu Gly Gln Val Glu Arg Phe Glu Thr Val Gly Met Glu Ala Ala
                725                 730                 735

Thr Asp Glu Gly Met Pro Lys Ser Tyr Leu Pro Gln Thr Val Arg Gln
            740                 745                 750

Gly Gly Tyr Met Pro Gln
        755

<210> SEQ ID NO 3
<211> LENGTH: 1842
<212> TYPE: DNA
<213> ORGANISM: human
<220> FEATURE:
<221> NAME/KEY: CDS
<222> LOCATION: (1)..(1842)
<223> OTHER INFORMATION:

<400> SEQUENCE: 3 atg gtt ctt gcc agc tct acc acc agc atc cac acc atg ctg ctc ctg    48
Met Val Leu Ala Ser Ser Thr Thr Ser Ile His Thr Met Leu Leu Leu
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
ctc ctg atg ctc ttc cac ctg gga ctc caa gct tca atc tcg gcg cgc    96
Leu Leu Met Leu Phe His Leu Gly Leu Gln Ala Ser Ile Ser Ala Arg
            20                  25                  30 cag gac tac aag gac gac gat gac aag acg cgc cag tct agt tca ggt   144
Gln Asp Tyr Lys Asp Asp Asp Asp Lys Thr Arg Gln Ser Ser Ser Gly
        35                  40                  45 tca aaa tta aaa gat cct gaa ctg agt tta aaa ggc acc cag cac atc   192
Ser Lys Leu Lys Asp Pro Glu Leu Ser Leu Lys Gly Thr Gln His Ile
50                  55                  60 atg caa gca ggc cag aca ctg cat ctc caa tgc agg ggg gaa gca gcc   240
Met Gln Ala Gly Gln Thr Leu His Leu Gln Cys Arg Gly Glu Ala Ala
 65                  70                  75                  80 cat aaa tgg tct ttg cct gaa atg gtg agt aag gaa agc gaa agg ctg   288
His Lys Trp Ser Leu Pro Glu Met Val Ser Lys Glu Ser Glu Arg Leu
                85                  90                  95 agc ata act aaa tct gcc tgt gga aga aat ggc aaa caa ttc tgc agt   336
Ser Ile Thr Lys Ser Ala Cys Gly Arg Asn Gly Lys Gln Phe Cys Ser
            100                 105                 110 act tta acc ttg aac aca gct caa gca aac cac act ggc ttc tac agc   384
Thr Leu Thr Leu Asn Thr Ala Gln Ala Asn His Thr Gly Phe Tyr Ser
        115                 120                 125 tgc aaa tat cta gct gta cct act tca aag aag aag gaa aca gaa tct   432
Cys Lys Tyr Leu Ala Val Pro Thr Ser Lys Lys Lys Glu Thr Glu Ser
130                 135                 140 gca atc tat ata ttt att agt gat aca ggt aga cct ttc gta gag atg   480
Ala Ile Tyr Ile Phe Ile Ser Asp Thr Gly Arg Pro Phe Val Glu Met
145                 150                 155                 160 tac agt gaa atc ccc gaa att ata cac atg act gaa gga agg gag ctc   528
Tyr Ser Glu Ile Pro Glu Ile Ile His Met Thr Glu Gly Arg Glu Leu
                165                 170                 175 gtc att ccc tgc cgg gtt acg tca cct aac atc act gtt act tta aaa   576
Val Ile Pro Cys Arg Val Thr Ser Pro Asn Ile Thr Val Thr Leu Lys
            180                 185                 190 aag ttt cca ctt gac act ttg atc cct gat gga aaa cgc ata atc tgg   624
Lys Phe Pro Leu Asp Thr Leu Ile Pro Asp Gly Lys Arg Ile Ile Trp
        195                 200                 205 gac agt aga aag ggc ttc atc ata tca aat gca acg tac aaa gaa ata   672
Asp Ser Arg Lys Gly Phe Ile Ile Ser Asn Ala Thr Tyr Lys Glu Ile
210                 215                 220 ggg ctt ctg acc tgt gaa gca aca gtc aat ggg cat ttg tat aag aca   720
Gly Leu Leu Thr Cys Glu Ala Thr Val Asn Gly His Leu Tyr Lys Thr
225                 230                 235                 240 aac acg aga gtt caa atg acc tgg agt tac cct gat gaa aaa aat aag   768
Asn Thr Arg Val Gln Met Thr Trp Ser Tyr Pro Asp Glu Lys Asn Lys
                245                 250                 255 aga gct tcc gta agg cga cga att gac caa agc aat tcc cat gcc aac   816
Arg Ala Ser Val Arg Arg Arg Ile Asp Gln Ser Asn Ser His Ala Asn
            260                 265                 270 ata ttc tac agt gtt ctt act att gac aaa atg cag aac aaa gac aaa   864
Ile Phe Tyr Ser Val Leu Thr Ile Asp Lys Met Gln Asn Lys Asp Lys
        275                 280                 285 gga ctt tat act tgt cgt gta agg agt gga cca tca ttc aaa tct gtt   912
Gly Leu Tyr Thr Cys Arg Val Arg Ser Gly Pro Ser Phe Lys Ser Val
290                 295                 300 aac acc tca gtg cat ata gga gaa att gaa gcc ata gtc gtg cct gtt   960
Asn Thr Ser Val His Ile Gly Glu Ile Glu Ala Ile Val Val Pro Val
305                 310                 315                 320 tgc tta gca ttc cta atg aca act ctt ctg gga gtg ctg ttc tgc ttt  1008
```

| | | |
|---|---|---|
| Cys Leu Ala Phe Leu Leu Thr Thr Leu Leu Gly Val Leu Phe Cys Phe<br>　　　　　　325　　　　　　　　　　330　　　　　　　　　　335 | | |
| aat aag cga gac cta att aaa aaa cac atc tgg cct aat gtt cca gat<br>Asn Lys Arg Asp Leu Ile Lys Lys His Ile Trp Pro Asn Val Pro Asp<br>　　　　　340　　　　　　　　　　345　　　　　　　　　　350 | | 1056 |
| cct tca aag agt cat att gcc cag tgg tca cct cac act cct cca agg<br>Pro Ser Lys Ser His Ile Ala Gln Trp Ser Pro His Thr Pro Pro Arg<br>355　　　　　　　　　　360　　　　　　　　　　365 | | 1104 |
| cac aat ttt aat tca aaa gat caa atg tat tca gat ggc aat ttc act<br>His Asn Phe Asn Ser Lys Asp Gln Met Tyr Ser Asp Gly Asn Phe Thr<br>　　370　　　　　　　　　　375　　　　　　　　　　380 | | 1152 |
| gat gta agt gtt gtg gaa ata gaa gca aat gac aaa aag cct ttt cca<br>Asp Val Ser Val Val Glu Ile Glu Ala Asn Asp Lys Lys Pro Phe Pro<br>385　　　　　　　　　　390　　　　　　　　　　395　　　　　　　　　　400 | | 1200 |
| gaa gat ctg aaa tta ttg gac ctg ttc aaa aag gaa aaa att aat act<br>Glu Asp Leu Lys Leu Leu Asp Leu Phe Lys Lys Glu Lys Ile Asn Thr<br>　　　　　　　　　　405　　　　　　　　　　410　　　　　　　　　　415 | | 1248 |
| gaa gga cac agc agt ggt att ggg ggg tct tca tgc atg tca tct tct<br>Glu Gly His Ser Ser Gly Ile Gly Gly Ser Ser Cys Met Ser Ser Ser<br>　　　　　420　　　　　　　　　　425　　　　　　　　　　430 | | 1296 |
| agg cca agc att tct agc agt gat gaa aat gaa tct tca caa aac act<br>Arg Pro Ser Ile Ser Ser Ser Asp Glu Asn Glu Ser Ser Gln Asn Thr<br>435　　　　　　　　　　440　　　　　　　　　　445 | | 1344 |
| tcg agc act gtc cag tat tct acc gtg gta cac agt ggc tac aga cac<br>Ser Ser Thr Val Gln Tyr Ser Thr Val Val His Ser Gly Tyr Arg His<br>　　450　　　　　　　　　　455　　　　　　　　　　460 | | 1392 |
| caa gtt ccg tca gtc caa gtc ttc tca aga tcc gag tct acc cag ccc<br>Gln Val Pro Ser Val Gln Val Phe Ser Arg Ser Glu Ser Thr Gln Pro<br>465　　　　　　　　　　470　　　　　　　　　　475　　　　　　　　　　480 | | 1440 |
| ttg tta gat tca gag gag cgg cca gaa gat cta caa tta gta gat cat<br>Leu Leu Asp Ser Glu Glu Arg Pro Glu Asp Leu Gln Leu Val Asp His<br>　　　　　　　　　　485　　　　　　　　　　490　　　　　　　　　　495 | | 1488 |
| gta gat ggc ggt gat ggt att ttg ccc agg caa cag tac ttc aaa cag<br>Val Asp Gly Gly Asp Gly Ile Leu Pro Arg Gln Gln Tyr Phe Lys Gln<br>　　　　　500　　　　　　　　　　505　　　　　　　　　　510 | | 1536 |
| aac tgc agt cag cat gaa tcc agt cca gat att tca cat ttt gaa agg<br>Asn Cys Ser Gln His Glu Ser Ser Pro Asp Ile Ser His Phe Glu Arg<br>515　　　　　　　　　　520　　　　　　　　　　525 | | 1584 |
| tca aag caa gtt tca tca gtc aat gag gaa gat ttt gtt aga ctt aaa<br>Ser Lys Gln Val Ser Ser Val Asn Glu Glu Asp Phe Val Arg Leu Lys<br>　　530　　　　　　　　　　535　　　　　　　　　　540 | | 1632 |
| cag cag att tca gat cat att tca caa tcc tgt gga tct ggg caa atg<br>Gln Gln Ile Ser Asp His Ile Ser Gln Ser Cys Gly Ser Gly Gln Met<br>545　　　　　　　　　　550　　　　　　　　　　555　　　　　　　　　　560 | | 1680 |
| aaa atg ttt cag gaa gtt tct gca gca gat gct ttt ggt cca ggt act<br>Lys Met Phe Gln Glu Val Ser Ala Ala Asp Ala Phe Gly Pro Gly Thr<br>　　　　　　　　　　565　　　　　　　　　　570　　　　　　　　　　575 | | 1728 |
| gag gga caa gta gaa aga ttt gaa aca gtt ggc atg gag gct gcg act<br>Glu Gly Gln Val Glu Arg Phe Glu Thr Val Gly Met Glu Ala Ala Thr<br>　　　　　580　　　　　　　　　　585　　　　　　　　　　590 | | 1776 |
| gat gaa ggc atg cct aaa agt tac tta cca cag act gta cgg caa ggc<br>Asp Glu Gly Met Pro Lys Ser Tyr Leu Pro Gln Thr Val Arg Gln Gly<br>595　　　　　　　　　　600　　　　　　　　　　605 | | 1824 |
| ggc tac atg cct cag tga<br>Gly Tyr Met Pro Gln<br>　　610 | | 1842 |

<210> SEQ ID NO 4
<211> LENGTH: 613
<212> TYPE: PRT

```
<213> ORGANISM: human

<400> SEQUENCE: 4

Met Val Leu Ala Ser Ser Thr Ser Ile His Thr Met Leu Leu Leu
1               5                   10                  15

Leu Leu Met Leu Phe His Leu Gly Leu Gln Ala Ser Ile Ser Ala Arg
            20                  25                  30

Gln Asp Tyr Lys Asp Asp Asp Lys Thr Arg Gln Ser Ser Ser Gly
        35                  40                  45

Ser Lys Leu Lys Asp Pro Glu Leu Ser Leu Lys Gly Thr Gln His Ile
    50                  55                  60

Met Gln Ala Gly Gln Thr Leu His Leu Gln Cys Arg Gly Glu Ala Ala
65                  70                  75                  80

His Lys Trp Ser Leu Pro Glu Met Val Ser Lys Glu Ser Glu Arg Leu
                85                  90                  95

Ser Ile Thr Lys Ser Ala Cys Gly Arg Asn Gly Lys Gln Phe Cys Ser
                100                 105                 110

Thr Leu Thr Leu Asn Thr Ala Gln Ala Asn His Thr Gly Phe Tyr Ser
            115                 120                 125

Cys Lys Tyr Leu Ala Val Pro Thr Ser Lys Lys Lys Glu Thr Glu Ser
        130                 135                 140

Ala Ile Tyr Ile Phe Ile Ser Asp Thr Gly Arg Pro Phe Val Glu Met
145                 150                 155                 160

Tyr Ser Glu Ile Pro Glu Ile Ile His Met Thr Glu Gly Arg Glu Leu
                165                 170                 175

Val Ile Pro Cys Arg Val Thr Ser Pro Asn Ile Thr Val Thr Leu Lys
                180                 185                 190

Lys Phe Pro Leu Asp Thr Leu Ile Pro Asp Gly Lys Arg Ile Ile Trp
            195                 200                 205

Asp Ser Arg Lys Gly Phe Ile Ile Ser Asn Ala Thr Tyr Lys Glu Ile
210                 215                 220

Gly Leu Leu Thr Cys Glu Ala Thr Val Asn Gly His Leu Tyr Lys Thr
225                 230                 235                 240

Asn Thr Arg Val Gln Met Thr Trp Ser Tyr Pro Asp Glu Lys Asn Lys
                245                 250                 255

Arg Ala Ser Val Arg Arg Arg Ile Asp Gln Ser Asn Ser His Ala Asn
                260                 265                 270

Ile Phe Tyr Ser Val Leu Thr Ile Asp Lys Met Gln Asn Lys Asp Lys
            275                 280                 285

Gly Leu Tyr Thr Cys Arg Val Arg Ser Gly Pro Ser Phe Lys Ser Val
        290                 295                 300

Asn Thr Ser Val His Ile Gly Glu Ile Glu Ala Ile Val Val Pro Val
305                 310                 315                 320

Cys Leu Ala Phe Leu Leu Thr Thr Leu Leu Gly Val Leu Phe Cys Phe
                325                 330                 335

Asn Lys Arg Asp Leu Ile Lys Lys His Ile Trp Pro Asn Val Pro Asp
            340                 345                 350

Pro Ser Lys Ser His Ile Ala Gln Trp Ser Pro His Thr Pro Pro Arg
        355                 360                 365

His Asn Phe Asn Ser Lys Asp Gln Met Tyr Ser Asp Gly Asn Phe Thr
    370                 375                 380

Asp Val Ser Val Val Glu Ile Glu Ala Asn Asp Lys Lys Pro Phe Pro
385                 390                 395                 400
```

-continued

```
Glu Asp Leu Lys Leu Leu Asp Leu Phe Lys Lys Glu Lys Ile Asn Thr
            405                 410                 415
Glu Gly His Ser Ser Gly Ile Gly Gly Ser Ser Cys Met Ser Ser Ser
        420                 425                 430
Arg Pro Ser Ile Ser Ser Ser Asp Glu Asn Glu Ser Ser Gln Asn Thr
    435                 440                 445
Ser Ser Thr Val Gln Tyr Ser Thr Val Val His Ser Gly Tyr Arg His
450                 455                 460
Gln Val Pro Ser Val Gln Val Phe Ser Arg Ser Glu Ser Thr Gln Pro
465                 470                 475                 480
Leu Leu Asp Ser Glu Glu Arg Pro Glu Asp Leu Gln Leu Val Asp His
                485                 490                 495
Val Asp Gly Gly Asp Gly Ile Leu Pro Arg Gln Gln Tyr Phe Lys Gln
            500                 505                 510
Asn Cys Ser Gln His Glu Ser Ser Pro Asp Ile Ser His Phe Glu Arg
        515                 520                 525
Ser Lys Gln Val Ser Ser Val Asn Glu Glu Asp Phe Val Arg Leu Lys
    530                 535                 540
Gln Gln Ile Ser Asp His Ile Ser Gln Ser Cys Gly Ser Gly Gln Met
545                 550                 555                 560
Lys Met Phe Gln Glu Val Ser Ala Ala Asp Ala Phe Gly Pro Gly Thr
                565                 570                 575
Glu Gly Gln Val Glu Arg Phe Glu Thr Val Gly Met Glu Ala Ala Thr
            580                 585                 590
Asp Glu Gly Met Pro Lys Ser Tyr Leu Pro Gln Thr Val Arg Gln Gly
        595                 600                 605
Gly Tyr Met Pro Gln
    610

<210> SEQ ID NO 5
<211> LENGTH: 34
<212> TYPE: DNA
<213> ORGANISM: artificial sequence
<220> FEATURE:
<223> OTHER INFORMATION: 5' oligo

<400> SEQUENCE: 5
cacggatccg cagcacacta tcaccagagg aaag                              34

<210> SEQ ID NO 6
<211> LENGTH: 34
<212> TYPE: DNA
<213> ORGANISM: artificial sequence
<220> FEATURE:
<223> OTHER INFORMATION: 3' oligo

<400> SEQUENCE: 6
gcataagctt tcactttttt ttaggtctgc attc                              34

<210> SEQ ID NO 7
<211> LENGTH: 38
<212> TYPE: DNA
<213> ORGANISM: artificial sequence
<220> FEATURE:
<223> OTHER INFORMATION: 5' oligo

<400> SEQUENCE: 7
atatggcgcg cctagtcagc tactgggaca ccggggtc                          38
```

-continued

```
<210> SEQ ID NO 8
<211> LENGTH: 55
<212> TYPE: DNA
<213> ORGANISM: artificial sequence
<220> FEATURE:
<223> OTHER INFORMATION: 3' oligo (domains 1 to 4)

<400> SEQUENCE: 8
caggcacgac tatggcttca atttctccgg cctttcgta aatctgggtt ttcac        55

<210> SEQ ID NO 9
<211> LENGTH: 52
<212> TYPE: DNA
<213> ORGANISM: artificial sequence
<220> FEATURE:
<223> OTHER INFORMATION: 3' oligo (domains 1 to 3)

<400> SEQUENCE: 9
cacgactatg gcttcaattt ctcctatatg cactgaggtg ttaacagatt tg          52

<210> SEQ ID NO 10
<211> LENGTH: 37
<212> TYPE: DNA
<213> ORGANISM: artificial sequence
<220> FEATURE:
<223> OTHER INFORMATION: 5' oligo

<400> SEQUENCE: 10
acgtacgcgt tcactgaggc atgtagccgc cttgccg                           37

<210> SEQ ID NO 11
<211> LENGTH: 38
<212> TYPE: DNA
<213> ORGANISM: artificial sequence
<220> FEATURE:
<223> OTHER INFORMATION: 3' oligo

<400> SEQUENCE: 11
ggagaaattg aagccatagt cgtgcctgtt tgcttagc                          38
```

The invention claimed is:

1. An isolated monoclonal antibody or an antigen-binding fragment thereof which binds to human VEGF-B, wherein said antibody is 2H10 produced by the hybridoma deposited at the American Type Culture Collection (ATCC) as PTA-6889, and the binding of the antibody or the fragment thereof to human VEGF-B antagonizes binding between human VEGF-B and VEGF-R1.

2. An isolated chimeric antibody or an antigen-binding fragment thereof which binds to human VEGF-B, and the binding of the antibody or the fragment thereof to human VEGF-B antagonizes binding between human VEGF-B and VEGF-R1 wherein said antibody comprises a variable region that is the same as the variable region of monoclonal antibody 2H10 produced by the hybridoma deposited at the American Type Culture Collection (ATCC) as PTA-6889, fused to a constant region of a human antibody.

3. An isolated monoclonal antibody or an antigen-binding fragment thereof which binds to human VEGF-B, and the binding of the antibody or the fragment thereof to human VEGF-B antagonizes binding between human VEGF-B and VEGF-R1 wherein said antibody is a humanized form of monoclonal antibody 2H10 produced by the hybridoma deposited at the American Type Culture Collection (ATCC) as PTA-6889.

4. The isolated antibody or the antigen-binding fragment according to any one of claims 1, 2 or 3, wherein the antibody fragment is an Fv, Fab', or F(ab')$_2$ fragment or a single chain form thereof.

5. A composition comprising the isolated antibody or the antigen-binding fragment according to any one of claims 1, 2 or 3, and a pharmaceutically acceptable carrier.

6. The composition of claim 5, wherein the antibody fragment is an Fv, Fab', or F(ab')$_2$ fragment or a single chain form thereof.

* * * * *